(12) United States Patent
Tereshchenko et al.

(10) Patent No.: US 10,517,494 B2
(45) Date of Patent: Dec. 31, 2019

(54) METHOD AND SYSTEM TO ACCESS INAPPARENT CONDUCTION ABNORMALITIES TO IDENTIFY RISK OF VENTRICULAR TACHYCARDIA

(71) Applicants: Beth Israel Deaconess Medical Center, Inc., Boston, MA (US); Johns Hopkins University, Baltimore, MD (US); Oregon Health and Science University, Portland, OR (US)

(72) Inventors: Larisa G. Tereshchenko, Portland, OR (US); Mark E. Josephson, Boston, MA (US)

(73) Assignees: Beth Israel Deaconess Medical Center, Inc., Boston, MA (US); Johns Hopkins University, Baltimore, MD (US); Oregon Health and Science University, Portland, OR (US)

( * ) Notice: Subject to any disclaimer, the term of this patent is extended or adjusted under 35 U.S.C. 154(b) by 0 days.

(21) Appl. No.: 15/522,615

(22) PCT Filed: Nov. 13, 2015

(86) PCT No.: PCT/US2015/060734
§ 371 (c)(1),
(2) Date: Apr. 27, 2017

(87) PCT Pub. No.: WO2016/077790
PCT Pub. Date: May 19, 2016

(65) Prior Publication Data
US 2017/0332929 A1    Nov. 23, 2017

Related U.S. Application Data

(60) Provisional application No. 62/080,175, filed on Nov. 14, 2014.

(51) Int. Cl.
*A61B 5/04* (2006.01)
*A61B 5/0464* (2006.01)
(Continued)

(52) U.S. Cl.
CPC ........ *A61B 5/04011* (2013.01); *A61B 5/0464* (2013.01); *A61B 5/7275* (2013.01);
(Continued)

(58) Field of Classification Search
CPC .............. A61N 1/3622; G06K 9/00557; A61B 5/04011; A61B 5/0464; A61B 5/7275; A61B 5/7264
See application file for complete search history.

(56) References Cited

U.S. PATENT DOCUMENTS 6,480,734 B1   11/2002   Zhang et al.
6,760,615 B2   7/2004    Ferek-Petric
(Continued)

OTHER PUBLICATIONS

M.W. Kay, R.A. GrayMeasuring curvature and velocity vector fields for waves of cardiac excitation in 2-D media. IEEE Transactions on Biomedical Engineering ( vol. 52 , Issue: 1 , Jan. 2005) (Year: 2005).*
(Continued)

*Primary Examiner* — Amanda K Hulbert
*Assistant Examiner* — Natasha Patel
(74) *Attorney, Agent, or Firm* — Sterne, Kessler, Goldstein & Fox P.L.L.C.

(57) ABSTRACT

A method and system for determining a patient's risk of ventricular tachycardia are disclosed. The method includes receiving ECG signals from a patient and filtering the collected ECG signals to generate filtered ECG signals. The method further includes identifying a heart vector from the filtered ECG signals, and measuring a velocity of the heart vector movement. A change in curvature of the identified
(Continued)

heart vector movement is quantified and a risk of ventricular tachycardia is determined based at least on the measured velocity and the quantified change in curvature of the identified heart vector movement.

28 Claims, 25 Drawing Sheets

(51) Int. Cl.
    *A61B 5/00*           (2006.01)
    *A61N 1/362*         (2006.01)
    *G16H 50/30*         (2018.01)
    *G06K 9/00*           (2006.01)

(52) U.S. Cl.
    CPC ........... *A61N 1/3622* (2013.01); *G16H 50/30* (2018.01); *A61B 5/7264* (2013.01); *G06K 9/00557* (2013.01)

(56) References Cited

U.S. PATENT DOCUMENTS

| | | | |
|---|---|---|---|
| 7,904,153 B2 | 3/2011 | Greenhut et al. | |
| 8,209,002 B2 | 6/2012 | Vajdic et al. | |
| 8,457,721 B2 | 6/2013 | Desai | |
| 2004/0111021 A1* | 6/2004 | Olson | A61B 5/04011 600/407 |
| 2006/0116593 A1* | 6/2006 | Zhang | A61B 5/0452 600/512 |
| 2008/0058794 A1 | 3/2008 | Macadam et al. | |
| 2009/0088655 A1* | 4/2009 | Vajdic | A61B 5/04011 600/523 |
| 2010/0249626 A1* | 9/2010 | El Arab | A61B 5/04011 600/518 |
| 2011/0118803 A1* | 5/2011 | Hou | A61B 5/04011 607/17 |
| 2013/0079653 A1 | 3/2013 | Shim et al. | |
| 2016/0256063 A1* | 9/2016 | Friedman | A61B 5/04011 |

OTHER PUBLICATIONS

International Search Report dated Jan. 27, 2016 for Appl. No. PCT/US2015/060734, 2 pages.
Written Opinion of the International Search Authority dated Jan. 27, 2016 for Appl. No. PCT/US2015/060734, 6 pages.
International Preliminary Report on Patentability dated May 16, 2017 for Appl. No. PCT/US2015/060734, 7 pages.

* cited by examiner

METHOD AND SYSTEM TO ACCESS INAPPARENT CONDUCTION ABNORMALITIES TO IDENTIFY RISK OF VENTRICULAR TACHYCARDIA

STATEMENT REGARDING FEDERALLY-SPONSORED RESEARCH AND DEVELOPMENT

This invention was made with government support under Grant No. HL118277 awarded by the National Institutes of Health. The government has certain rights in the invention.

BACKGROUND

Field

Embodiments herein relate to systems and methods for analyzing electrocardiograms (ECG) to determine potential health risks.

Background

Cardiovascular disease, and in particular sudden cardiac death due to ventricular tachycardia, is the leading cause of death in the adult U.S. population. Sustained monomorphic ventricular tachycardia occurs in 1-2% of post-myocardial infarction patients. The risk for ventricular tachycardia is the highest in post-myocardial infarction patients with systolic heart failure. Nearly 5 million Americans are currently living with heart failure, and the burden of heart failure is increasing with the aging of the U.S. population. The mean age of those affected is in the mid 60's. An estimated 80% of instances of sudden cardiac death (SCD) are associated with coronary heart disease (CHD). SCD is the first clinical manifestation of the CHD in about half of SCD cases. It is beneficial to identify risk factors of SCD early in the natural history of conditions predisposing to SCD. Mechanisms of arrhythmic SCD have been extensively studied during the last 20 years, and data suggests that common underlying electrophysiological substrates could be found in all arrhythmic SCDs. However, knowledge of arrhythmogenic mechanisms has not been translated into the development of novel approaches to the analysis of the resting 12-lead ECG.

The implantable cardioverter-defibrillator (ICD) is currently used to help prevent sudden cardiac death in patients at risk of ventricular tachycardia (VT). However, the ICD cannot cure VT, and has a number of limitations. VT theoretically could be cured by VT ablation, however, VT recurrence after VT ablation is high.

The improvement of VT ablation techniques is limited by the absence of reliable operator-independent end-points of VT ablation. At present, non-inducibility of the clinical VT is used as an end-point for VT ablation. However, the inducibility end-point has a number of limitations: it cannot be used if clinical VT has not been adequately documented and discriminated from "non-clinical" VT; it cannot be used if VT was not-inducible before VT ablation; it increases procedural risk in patients with hemodynamically unstable VTs; LV systolic function and revascularization can influence predictive value of inducibility; VT "inducibility" is a probabilistic metric and therefore cannot be satisfactory reproducible; and the association between inducibility and recurrence of VT is inconsistent. Other end-points (elimination of late potentials and/or abnormal intracardiac electrograms), and combinations have been considered, but are operator-dependent.

BRIEF SUMMARY

Example methods and systems are described herein for embodying an approach to determine a patient's risk of ventricular tachycardia, and using the information to improve VT ablation techniques.

In an embodiment, an example method is described. The method includes receiving ECG signals from a patient. The ECG signals may be sensed from the patient and analyzed in real-time. Alternatively, the analysis may be done on ECG signals that were previously sensed from the patient and recorded (i.e., stored) for later analysis. The methods described herein for analyzing ECG signals may also be performed on collections of previously recorded ECG signals from various populations of patients. The method further includes filtering the collected ECG signals to generate filtered ECG signals, identifying a heart vector from the filtered ECG signals, and measuring a velocity of the heart vector. A change in curvature of the identified heart vector is quantified and a risk of ventricular tachycardia is determined based at least on the measured velocity and the quantified change in curvature of the identified heart vector.

In another embodiment, a system is described. The system includes an input module, a filtering module, and a processor. The input module receives ECG signals from a patient (either directly or previously recorded). The filtering module is configured to filter the received ECG signals to generate filtered ECG signals. The processor is configured to identify a heart vector from the filtered ECG signals, and measure a velocity of the heart vector. The processor is further configured to quantify a change in curvature of the identified heart vector.

In another embodiment, a computer program product stored on a computer readable media includes a set of instructions that, when executed by a computing device, perform the steps of: receiving ECG signals; identifying a heart vector from filtered ECG signals and measuring a velocity of the heart vector; quantifying a change in curvature of the identified heart vector; and determining a risk of ventricular tachycardia based at least on the measured velocity and the quantified change in curvature of the identified heart vector.

Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The patent or application file contains at least one drawing executed in color. Copies of this patent or patent application publication with color drawing(s) will be provided by the Office upon request and payment of the necessary fee.

The accompanying drawings, which are incorporated herein and form part of the specification, illustrate the present invention and, together with the description, further serve to explain the principles of the present invention and to enable a person skilled in the relevant art(s) to make and use the present invention.

Figure 1:
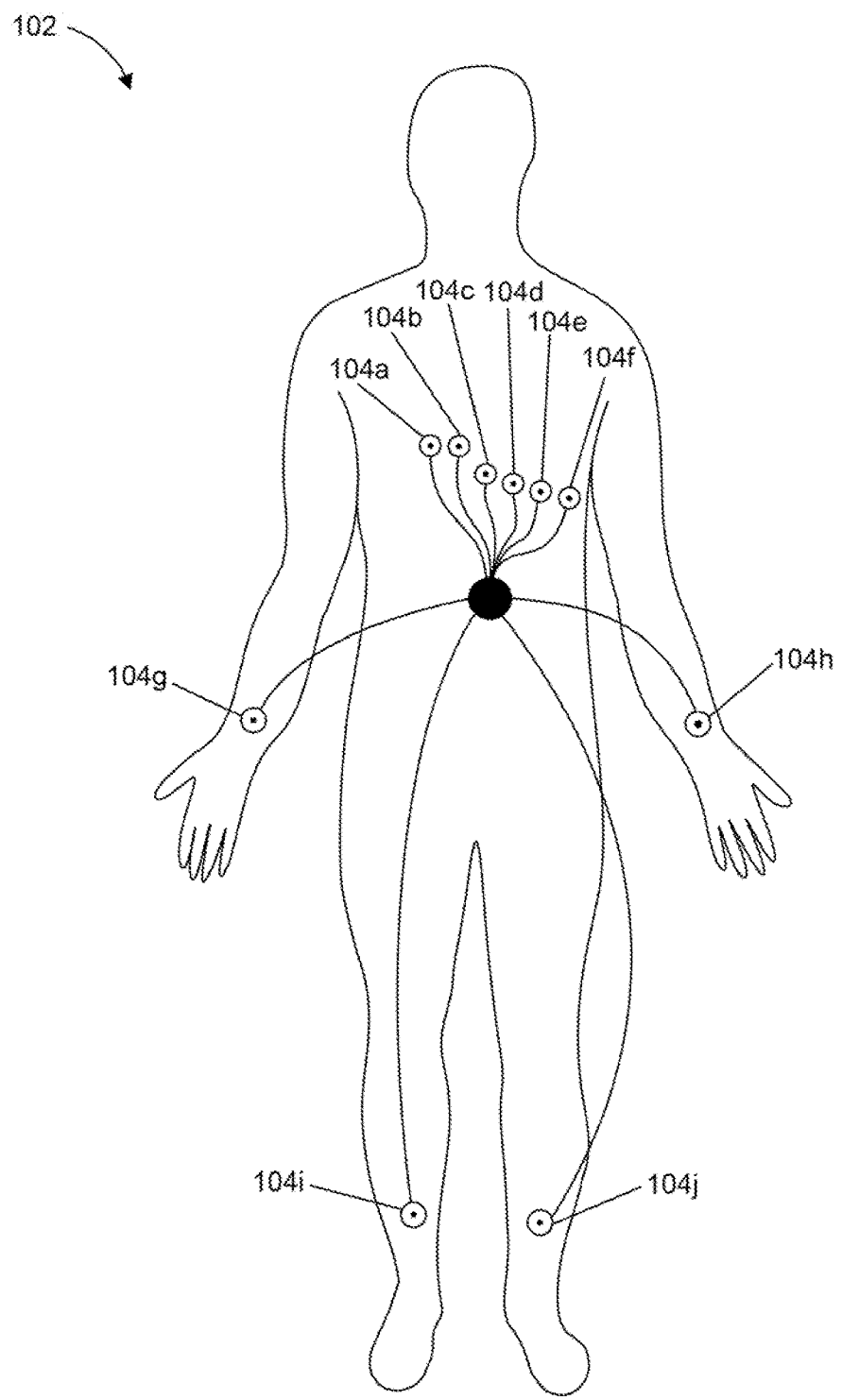
FIG. 1 illustrates leads of an ECG device placed on a patient, according to an embodiment.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

This specification discloses one or more embodiments that incorporate the features of this invention. The disclosed embodiment(s) merely exemplify the present invention. The scope of the present invention is not limited to the disclosed embodiment(s). The present invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 illustrates a patient 102 that is attached to various leads of an ECG recording device, according to an embodiment. The leads may be used to monitor a standard 12-lead ECG. In this example, six electrodes (leads 104a-f) may be placed across the chest of patient 102 while four other electrodes (leads 104g-j) are placed with two leads (104g and 104h) near the wrists and two leads (104i and 104j) near the ankles of patient 102.

It should be understood that the exact placement of the leads is not intended to be limiting. For example, the two lower leads 104i and 104j may be placed higher on the body, such as on the outer thighs. In another example, leads 104g and 104h are placed closer to the shoulders while leads 104i and 104j are placed closer to the hips of patient 102. In still other examples, not all ten leads are required to be used in order to monitor ECG signals from patient 102.

In an embodiment, signals are monitored from each of leads 104a-j during a standard 12-lead ECG recording. The ECG signals can be sensed from the patient and analyzed in real-time. Alternatively, the ECG signals can be recorded (i.e., stored) for later analysis. The resulting ECG signals may be analyzed over a single beat, or across multiple consecutive beats, to determine various health factors such as heart rate, strength of heart beat, and any indicators of abnormalities. Embodiments are described herein for performing the analysis on the received ECG signals to determine a risk of ventricular tachycardia. This analysis may also be used to improve the process of cardiac ablation by providing a more accurate location of damaged heart tissue to be ablated.

Figure 2:
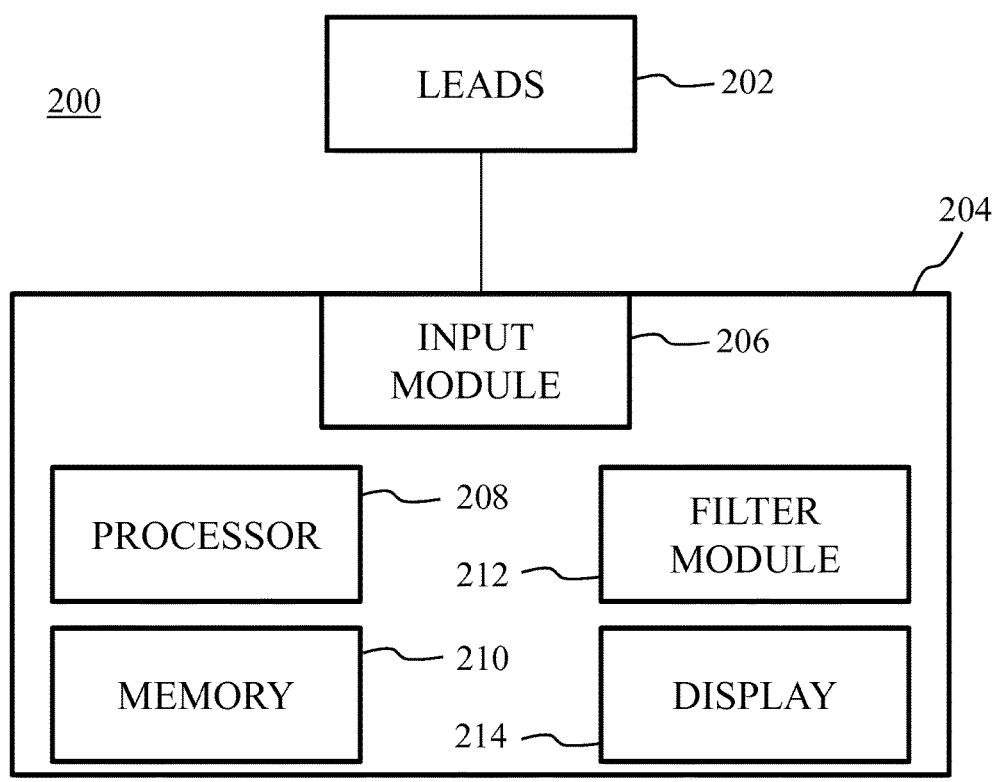
FIG. 2 illustrates an example ECG system, according to an embodiment.

FIG. 2 illustrates an example ECG system 200 for collecting and processing ECG signals, according to an embodiment. ECG system 200 may be used at a hospital or may be a portable device for use wherever the patient may be. In another example, ECG system 200 may be an implantable biomedical device with leads implanted in various locations around the body of a patient. ECG system 200 may be part of or may be coupled with other implantable biomedical devices such as a cardiac pacemaker, an implantable cardioverter-defibrillator (ICD) or a cardiac resynchronization therapy (CRT) device.

ECG system 200 includes leads 202 and a main unit 204. Leads 202 may comprise any number and type of electrical leads. For example, leads 202 may comprise ten electrodes to be used with a standard 12-lead ECG. Leads 202 may be similar to leads 104a-j as illustrated in FIG. 1 and described previously. In another example, leads 202 may comprise implanted electrical leads, such as insulated wires placed throughout the body. The implanted leads may be intracardiac leads placed in close proximity on the heart tissue of a patient. In another example, leads 202 may comprise a plurality of leads placed across a patient's body for collecting surface body potentials. In another example, leads 202 may include a set of XYZ leads, such as those commonly used for spatial vectorcardiography.

Main unit 204 may include an input module 206, a processor 208, a memory module 210, a filtering module 212, and a display 214. Input module 206 includes suitable circuitry and hardware to receive the signals from leads 202. As such, input module 206 may include components such as, for example, analog-to-digital converters, de-serializers, filters, and amplifiers. These various components may be implemented to condition the received signals to a more suitable form for further signal processing. Input module 206 may also be configured to receive pre-recorded ECG signal for further processing.

Filtering module 212 may be designed as either an analog or digital filter in order to filter the received ECG signals and generate filtered ECG signals, according to an embodiment. Filtering module 212 may be a part of processor 208 in the example where it is a digital filter.

Filtering module 212 may be a bandpass filter designed to provide a narrow passband of frequencies. For example, filtering module 212 may apply a passband having a bandwidth between 10 and 100 Hz. In one embodiment, the passband bandwidth is about 10 Hz. The passband may be incremented using, for example, 10 Hz intervals to filter different frequency regions of the received ECG signals.

Processor 208 may include one or more hardware microprocessor units. In an embodiment, processor 208 is configured to perform signal processing procedures on the signals received via input module 206. In another embodiment, processor 208 performs signal processing procedures on the ECG signals after they have been filtered by filtering module 212.

Processor 208 may identify a heart vector from the filtered ECG signals and measure a velocity of the heart vector. The heart vector may be determined from a three-dimensional representation of the filtered ECG signals such as a plot of the QRS loops. In other embodiments, plots of different regions of the heartbeat may be used, such as 'p' loops, or 't' loops. In an embodiment, the heart vector is established from an origin point in the plotted data and passes through various other points along the loop. A more detailed explanation of determining the heart vector and its origin point from the collected data is found in the article Sur et al., "Comparison of Sum Absolute QRST Integral, and Temporal Variability in Depolarization and Repolarization, Measured by Dynamic Vectorcardiography Approach, in Healthy Men and Women," PLOS One, vol. 8(2), February 2013, the disclosure of which is incorporated by reference herein in its entirety.

The heart vector may be identified across a single beat or across at least two consecutive beats. Similarly, a velocity of the heart vector may be measured across a single beat or across at least two consecutive beats. The velocity may define a change in measured potential over a given period of time. In one example embodiment, the change in potential is measured over a period of 10 ms to determine the velocity during that 10 ms period.

Processor 208 may also be capable of quantifying a change in curvature of the identified heart vector movement (e.g., the curvature of the loop or loops of the three dimensional data plots) over a single beat, or across at least two consecutive beats. This curvature change may be identified within a given time period, such as the same 10 ms time period used to measure the velocity. In one embodiment, the change in curvature is determined using standard pattern recognition algorithms to quantify the curvature change in a given timeframe. The heart vector velocity and curvature data may be used by processor 208 to determine a risk of ventricular tachycardia for the associated patient, according to an embodiment.

Processor 208 may also be capable of calculating a scalar measure of a rotation rate of the heart vector, known as orbital frequency. The orbital frequency is calculated by multiplying the velocity of the heart vector with the curvature of the heart vector, averaged over each QRS segment of the heart vector.

Table 1 below provides an example of various velocity values over a given frequency range and time period of the cardiac cycle. The mean and standard deviation of the measured velocities are shown for those patients that did not experience sudden cardiac death (SCD NO) vs. those patients that did experience sudden cardiac death (SCD YES). The velocities were measured over the 10 ms segments of the QRS loop. As can be seen in this example, the increase in measured heart vector velocity is a potential predictor of future VT events that can lead to SCD.

TABLE 1

| QRS Filter | QRS ms | SCD NO (n = 14,699) | SCD YES (n = 291) | P-value |
|---|---|---|---|---|
| Unfiltered | 10 ms | 18.4 ± 13.8 | 25.3 ± 20.8 | <0.0001 |
| Unfiltered | 20 ms | 43.0 ± 30.9 | 56.3 ± 39.3 | <0.0001 |
| Unfiltered | 30 ms | 94.6 ± 55.4 | 113.1 ± 68.2 | <0.0001 |
| Unfiltered | 40 ms | 127.6 ± 61.7 | 145.6 ± 68.4 | <0.0001 |
| Unfiltered | 50 ms | 139.8 ± 65.3 | 161.3 ± 81.9 | <0.0001 |
| Unfiltered | 60 ms | 129.6 ± 60.9 | 146.5 ± 71.3 | 0.0001 |
| Unfiltered | 70 ms | 90.4 ± 48.0 | 104.1 ± 51.7 | <0.0001 |
| Unfiltered | 80 ms | 60.6 ± 38.9 | 67.8 ± 40.9 | 0.003 |
| 70-300 Hz | 10 ms | 4.7 ± 2.5 | 5.8 ± 3.3 | <0.0001 |
| 70-300 Hz | 20 ms | 8.8 ± 3.9 | 10.3 ± 5.1 | <0.0001 |
| 70-300 HZ | 100 ms | 3.8 ± 2.9 | 4.3 ± 3.2 | <0.0001 |
| 70-300 HZ | 110 ms | 2.1 ± 1.9 | 2.5 ± 2.6 | <0.0001 |

Table 2 below provides an example of various quantified curvatures over a given frequency range and time period of the cardiac cycle. The mean and range of quantified curvatures are shown for those patients that did not experience sudden cardiac death (SCD NO) vs. those patients that did experience sudden cardiac death (SCD YES). As can be seen in this example, the lower quantified curvature values are a potential predictor of future VT events that can lead to SCD.

TABLE 2

| QRS Filter | QRS ms | SCD NO (n = 14,699) | SCD YES (n = 291) | P-value |
|---|---|---|---|---|
| Unfiltered | 10 ms | 0.13 (0.07-0.25) | 0.09 (0.04-0.19) | <0.0001 |
| Unfiltered | 20 ms | 0.07 (0.04-0.13) | 0.05 (0.02-0.10) | <0.0001 |
| 10-19 Hz | 10 ms | 0.008 (0.004-0.02) | 0.006 (0.003-0.014) | 0.0004 |
| 10-19 Hz | 20 ms | 0.023 (0.015-0.04) | 0.021 (0.013-0.033) | 0.002 |
| 50-59 Hz | 10 ms | 1.10 (0.79-1.46) | 0.93 (0.64-1.34) | <0.0001 |
| 50-59 Hz | 20 ms | 0.74 (0.55-1.00) | 0.65 (0.46-0.89) | <0.0001 |
| 50-59 Hz | 110 ms | 0.50 (0.36-0.67) | 0.46 (0.32-0.59) | 0.0001 |
| 50-59 Hz | 120 ms | 0.59 (0.41-0.81) | 0.51 (0.34-0.70) | <0.0001 |
| 60-69 Hz | 10 ms | 1.77 ± 0.77 | 1.55 ± 0.68 | <0.0001 |
| 60-69 Hz | 20 ms | 1.12 ± 0.50 | 0.99 ± 0.45 | <0.0001 |
| 60-69 Hz | 100 ms | 0.84 ± 0.37 | 0.74 ± 0.35 | <0.0001 |
| 60-69 Hz | 110 ms | 1.02 ± 0.49 | 0.88 ± 0.45 | <0.0001 |
| 70-300 Hz | 10 ms | 0.73 ± 0.31 | 0.62 ± 0.28 | <0.0001 |
| 70-300 Hz | 20 ms | 0.54 ± 0.22 | 0.47 ± 0.20 | <0.0001 |
| 70-300 Hz | 30 ms | 0.40 ± 0.15 | 0.35 ± 0.15 | <0.0001 |
| 70-300 Hz | 40 ms | 0.28 ± 0.11 | 0.26 ± 0.11 | 0.006 |
| 70-300 Hz | 70 ms | 0.29 ± 0.11 | 0.27 ± 0.10 | <0.0001 |

TABLE 2-continued

| QRS Filter | QRS ms | SCD NO (n = 14,699) | SCD YES (n = 291) | P-value |
|---|---|---|---|---|
| 70-300 Hz | 80 ms | 0.43 ± 0.15 | 0.37 ± 0.14 | <0.0001 |
| 70-300 Hz | 90 ms | 0.54 ± 0.21 | 0.45 ± 0.21 | <0.0001 |
| 70-300 Hz | 100 ms | 0.55 ± 0.29 | 0.47 ± 0.26 | <0.0001 |
| 70-300 Hz | 110 ms | 0.47 ± 0.34 | 0.41 ± 0.29 | 0.001 |

Processor 208 may be designed to provide the heart vector velocity and curvature data to display 214, or to an external device, according to another embodiment. Processor 208 may also comprise a field-programmable gate array (FPGA) that includes configurable logic. The configurable logic may be programmed to perform the various functions discussed above using configuration code stored in memory module 210. Likewise, processor 208 may be programmed via instructions stored in memory module 210.

Memory module 210 may include any type of memory including, for example, random access memory (RAM), read-only memory (ROM), electrically-erasable programmable read-only memory (EEPROM), FLASH memory, magnetic memory, optical memory, etc. Furthermore, memory module 210 may include both volatile and non-volatile memory. For example, memory module 210 may contain a set of coded instructions in non-volatile memory for programming processor 208. The filtered ECG signals may also be stored in either the volatile or non-volatile memory depending on how long retention is desired. Memory module 210 may also be used to save data related to the measured velocity of the identified heart vector, or the quantified change in curvature of the movement of the identified heart vector.

In an embodiment, main unit 204 includes display 214 for providing a visual representation of data. For example, display 214 may be used to display the received signals from leads 202. In another example, display 214 may be used to display the filtered ECG signals after being filtered by filtering module 212. In another example, display 214 may display the raw data related to heart vector velocity and curvature change calculated by processor 208. Display 812 may utilize any of a number of different display technologies such as, for example, liquid crystal display (LCD), light emitting diode (LED), plasma or cathode ray tube (CRT).

In one embodiment, display 214 may display a three dimensional representation of the filtered or unfiltered ECG data during a beat or across multiple beats. For example, display 214 may display QRS loops from the ECG data. The three dimensional representation can provide improved visualization of inapparent conduction occurring in the patient's heart beat rhythm, as well as various conduction paths across the beat or beats.

In another embodiment, processor 208 may use the measured velocity and change in curvature of the identified heart vector to localize an origin of arrhythmia in the patient's heart. Processor 208 may combine the data associated with the measured velocity and change in curvature of the identified heart vector with data from other cardiac imaging modalities, such as CT, MRI, etc., in order to localize an origin of arrhythmia. A more accurate localization of an arrhythmia may be used to improve the accuracy of cardiac ablation in an effort to cure ventricular tachycardia in a patient.

Figure 3:
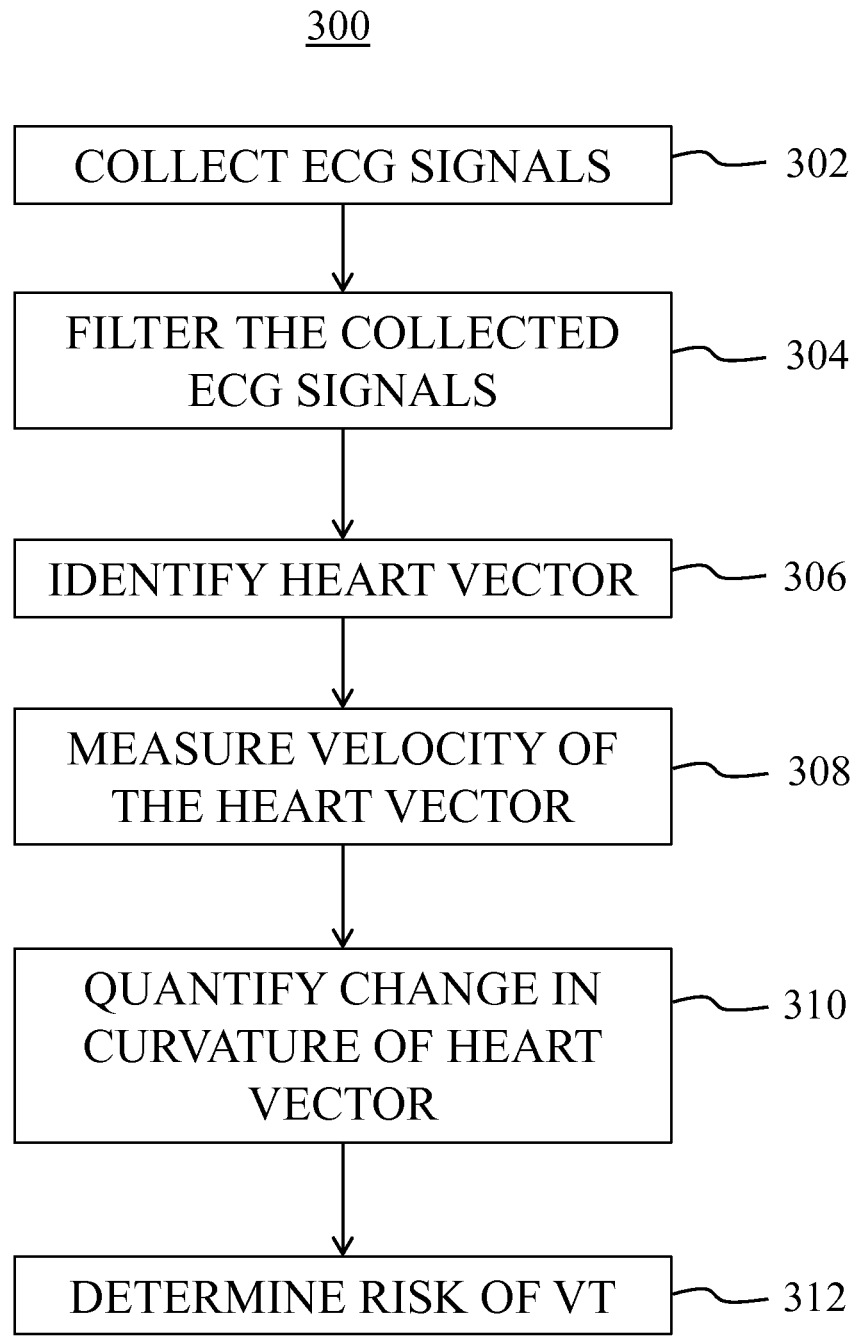
FIG. 3 illustrates an example method, according to an embodiment.

FIG. 3 illustrates a flowchart depicting a method 300 for identifying risk of ventricular tachycardia in a patient, according to an embodiment. Method 300 may be performed by the various components of ECG system 200. It is to be appreciated that method 300 may not include all operations shown or perform the operations in the order shown.

Method 300 starts at step 302 where ECG signals are collected, according to an embodiment. The ECG signals may be collected from various types of leads and lead configurations, such as a 12-lead ECG, a set of XYZ leads, implantable leads, etc. Surface body potentials may be collected as well using a plurality of leads placed across a patient's body. The plurality of leads used for collecting surface body potentials may include more than 200 leads. In another example, the plurality of leads used for collecting surface body potentials includes about 64 leads. The ECG signals may be collected across at least two consecutive heart beats of a patient.

The collected ECG signals may be used to plot QRS loops. According to an embodiment, a sampling frequency of at least 500 Hz is utilized when plotting the loops. In another example, a sampling frequency of at least 1000 Hz is utilized when plotting the loops.

At step 304, the collected ECG signals are filtered, according to an embodiment. The filtering may involve filtering each ECG signal from each lead, or may involve filtering some combined ECG signal that includes the signals from more than one lead. In an embodiment, the filtering includes a bandpass filtering operation having a bandwidth of about 10 Hz. Other narrow bandwidths may be considered as well. The bandpass frequency range may be shifted to analyze various frequency segments of the collected ECG signals. In one example, the bandpass frequency range may be shifted by 10 Hz increments.

The filtered ECG signals may be displayed. For example, QRS loops may be plotted in three spatial dimensions based on the filtered ECG data. Displaying such information may allow for visualization of inapparent conduction occurring in a patient's heart beat. A user may also use the displayed data to identify a heart vector to have its velocity and curvature change calculated over a given time period.

At step 306, a heart vector is identified from the filtered ECG signals, according to an embodiment. The heart vector may be identified by a processing device that is analyzing the filtered ECG signals, or via a user who could identify the heart vector based on a three dimensional image of the filtered ECG signals. For example, the user may indicate on a touchscreen, or via some other user interface, the location of the heart vector within an illustration of the QRS loops.

At step 308, a velocity of the heart vector is measured, according to an embodiment. The velocity may be measured across a single heart beat from the patient, or across at least two consecutive heart beats from the patient. The velocity may be measured by a processing device that is analyzing the filtered ECG signals.

At step 310, a change in curvature of the heart vector is quantified, according to an embodiment. The curvature change may be quantified across a single heart beat from the patient, or across at least two consecutive heart beats from the patient. The curvature change may be quantified by a processing device that is analyzing the filtered ECG signals.

At step 312, a risk of VT is identified for the given patient based at least on the measured velocity and quantified change in curvature of the identified heart vector, according to an embodiment. For example, if a patient's measured heart vector velocity for a given frequency range and over a given time period is above a certain threshold, then the patient is considered to be at increased risk for a VT event. Alternatively, or in addition, if the quantified curvature from the patient's heart vector is below a certain threshold, then the patient is considered to be at increased risk for a VT event. This data may also be used to identify specific areas within the heart that display abnormal conduction. In one embodiment, this data is merged with other imaging modality data acquired from CT or MRI scans, to name a few examples, in order to localize origins of arrhythmia in a patient's heart. Knowledge of these localized regions may aid in the cardiac ablation process to remove the damaged heart tissue.

Method 300 may include the collection of other data as well for the purpose of identifying VT risk in a patient. For example, surface body potentials may be measured from a plurality of leads placed across a patient. The data collected from the measured surface body potentials may be combined with the data collected from the filtered ECG signals in order to visualize a full three dimensional (endocardial, midmyocardial, epicardial) activation of the heart, according to an embodiment. Furthermore, this combined data may be used to help determine a risk factor for VT in the patient.

EXPERIMENTAL EXAMPLES

Provided herein are various examples of collected data, and its analysis, for determining VT risk in a population of patients. These examples are not intended to limit the scope or spirit of the invention in any way.

Experiment #1

A community dwelling cohort was studied. Participants with paced rhythm, atrial fibrillation, prevalent coronary heart disease (CHD), heart failure, and QRS duration ≥120 ms were excluded. The remaining CHD-free participants (n=13,368, mean age 53.9±5.7 ms; 56.5% female; 73.2% white) were analyzed. A baseline resting 12-lead ECG was transformed into an orthogonal XYZ ECG where only sinus beats were analyzed. The ECG signal was filtered (passband frequency between 40-49 Hz), and the filtered QRS loop length was measured. The velocity was calculated as the potential change of the filtered heart vector over each 10 ms of QRS length, divided by time. During a median follow up of 14 years, 183 participants died of sudden cardiac death (SCD). An unadjusted Cox regression velocity at 110-119 ms (continuous variable HR 1.42; 95% CI 1.29-1.57) and a velocity at 100-109 ms (HR1.14; 95% CI 1.07-1.21) were associated with those participants with SCD. After adjustment for age, sex, CHD risk factors (total cholesterol, triglycerides, high density lipoprotein, current smoking, diabetes, body mass index, leisure activity index, systolic blood pressure, use of antihypertensive drugs), QT-prolonging drugs, ECG characteristics (heart rate, QRS duration, QTc, QRS-T angle, sex-specific Cornell product), and stratified by race and study center, 110-119 ms velocity (HR 1.21; 95% CI 1.08-1.36) and 100-109 ms velocity (HR 1.09; 95% CI 1.02-1.16) remained a significant predictor of SCD. Thus, velocity of the heart vector movement through a terminal 20 ms of the filtered QRS loop is independently associated with SCD in a community-dwelling cohort of CHD-free adults.

Experiment #2

Figure 4A:
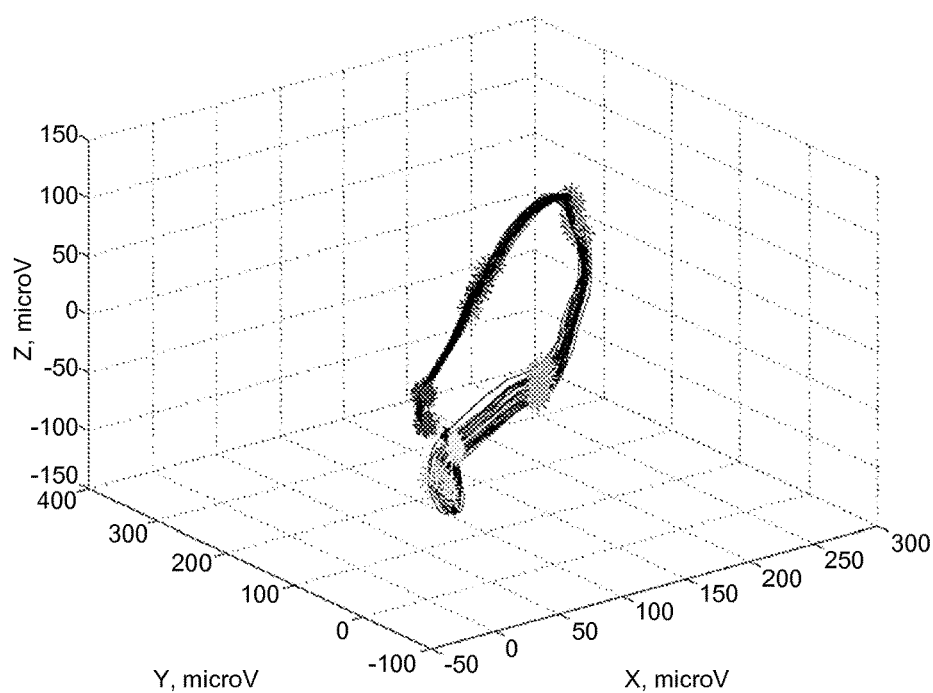
FIGS. 4A-4K illustrate example QRS loops from patients.
Figure 4B:
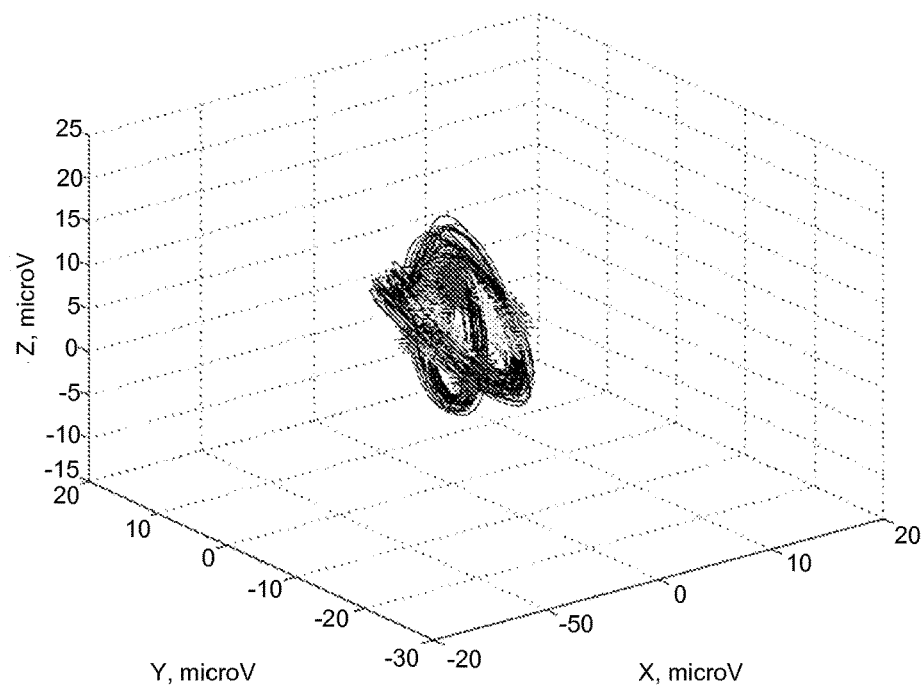
Figure 4C:
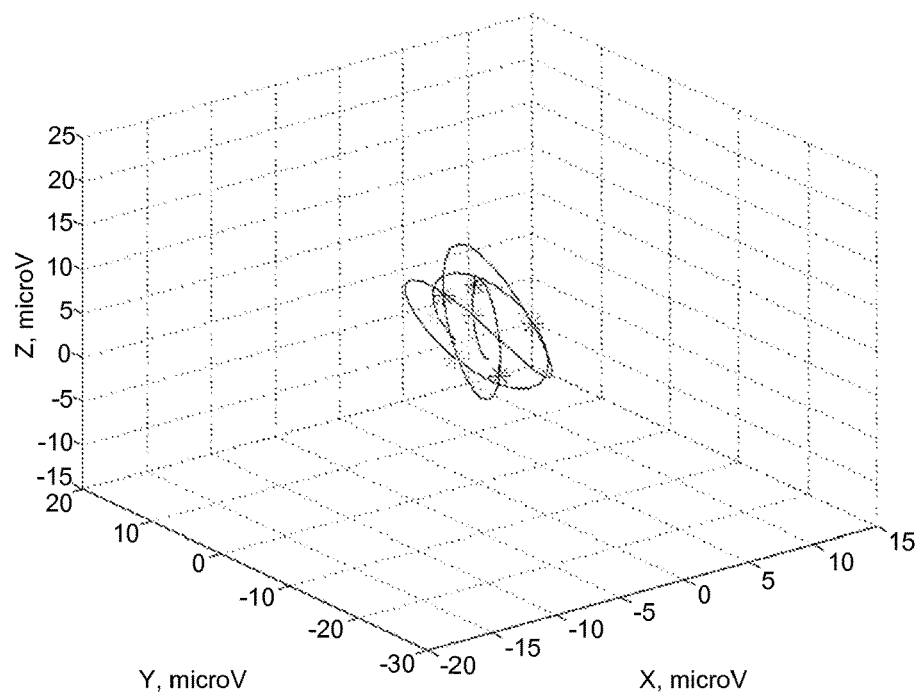
Figure 4D:
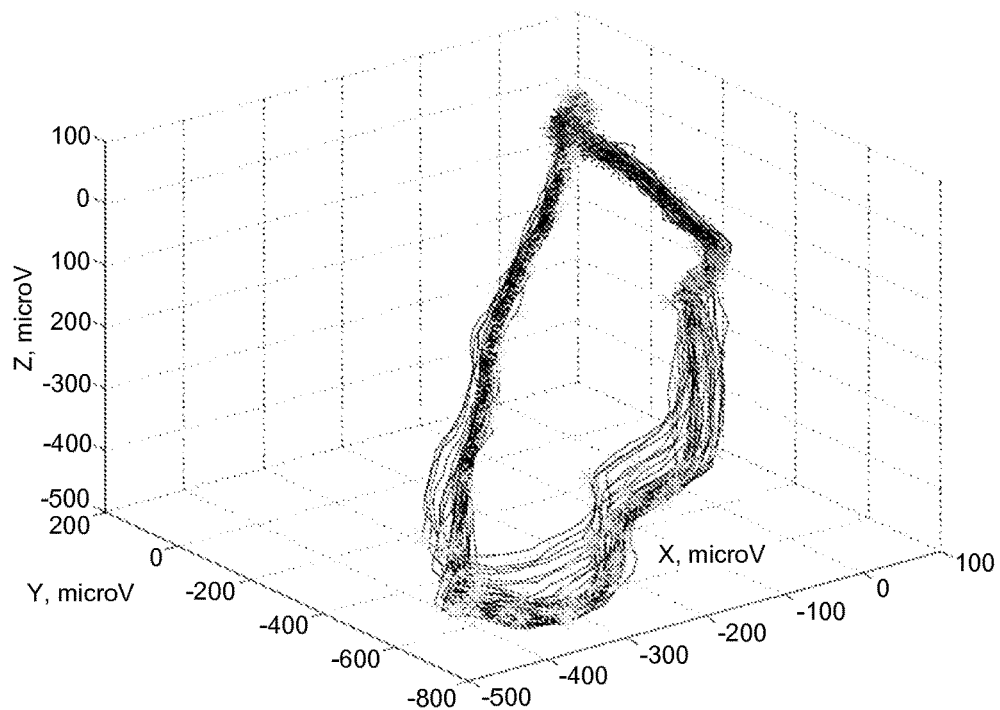
Figure 4E:
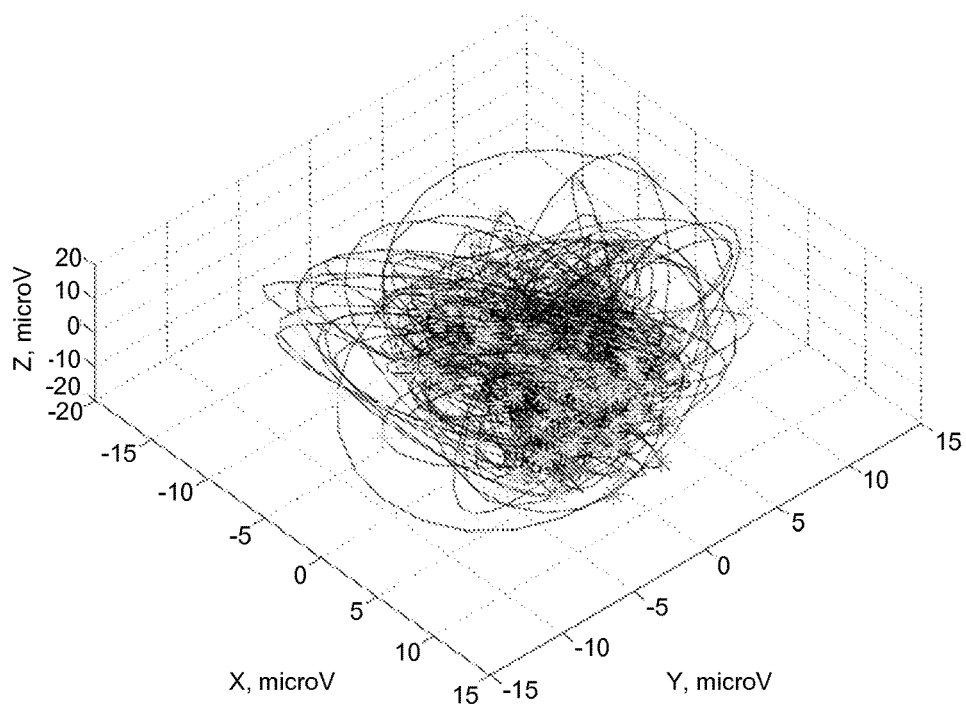
Figure 4F:
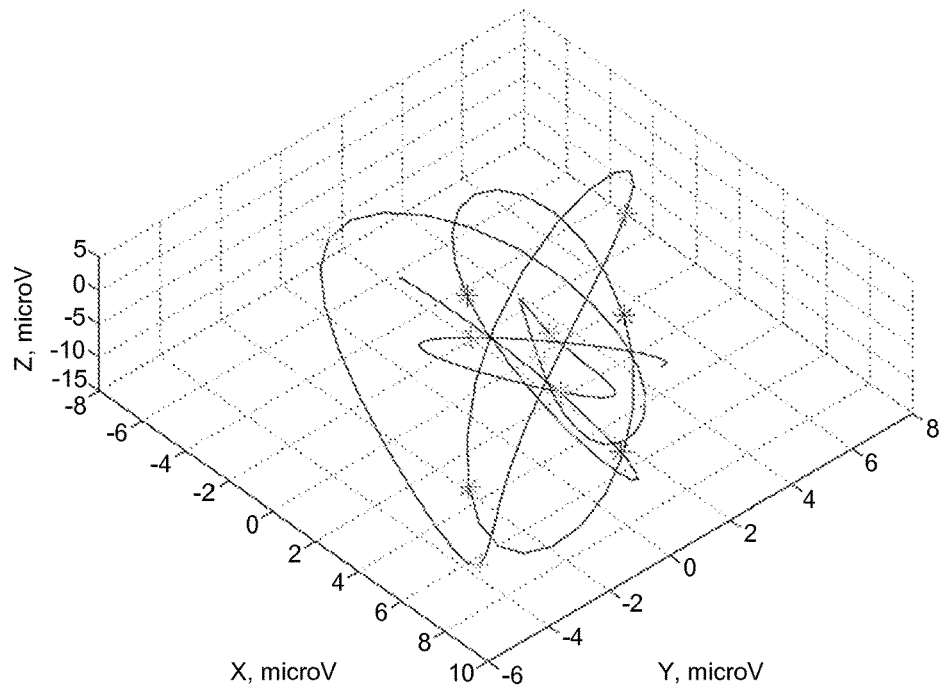
Figure 4G:
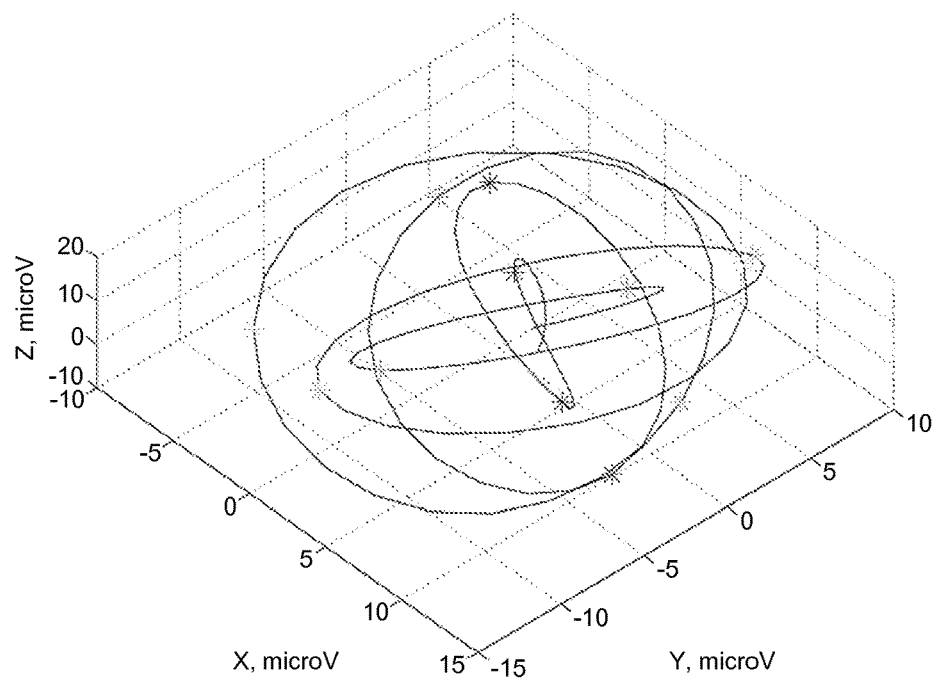
Figure 4H:
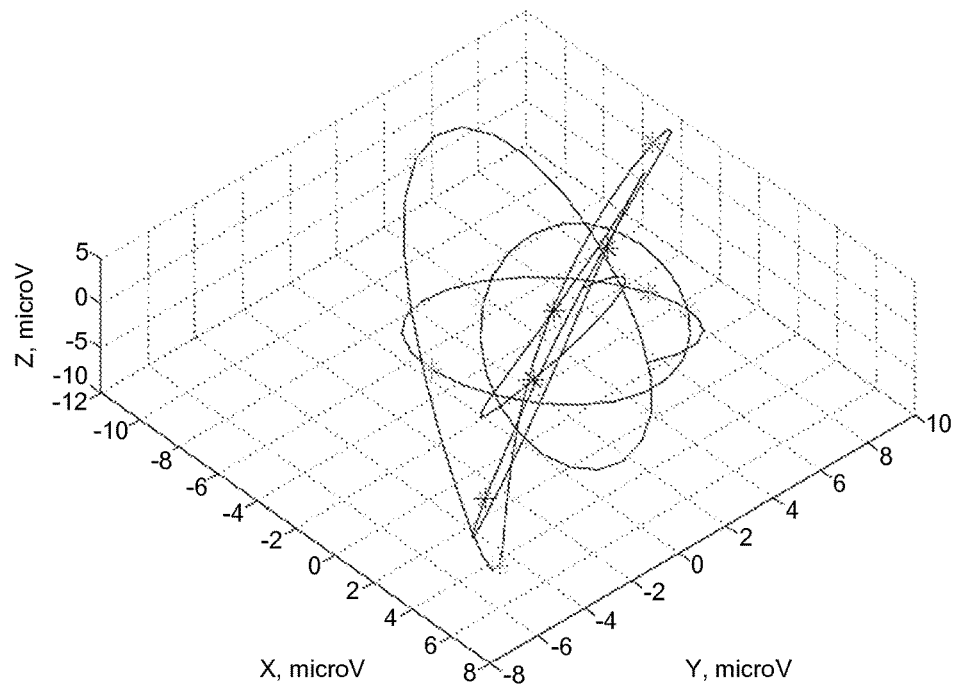
Figure 4I:
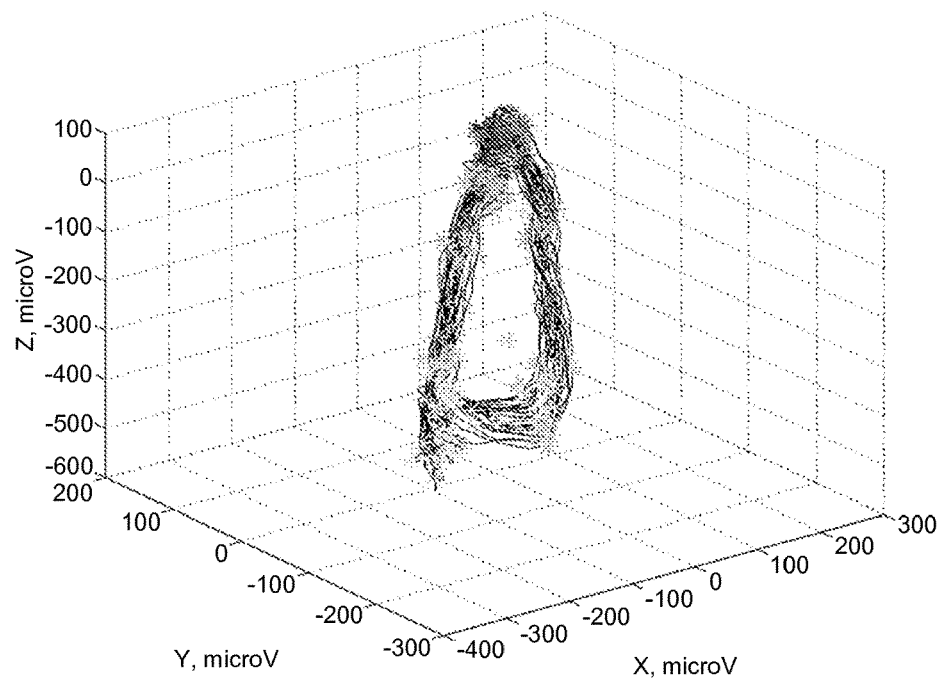
Figure 4J:
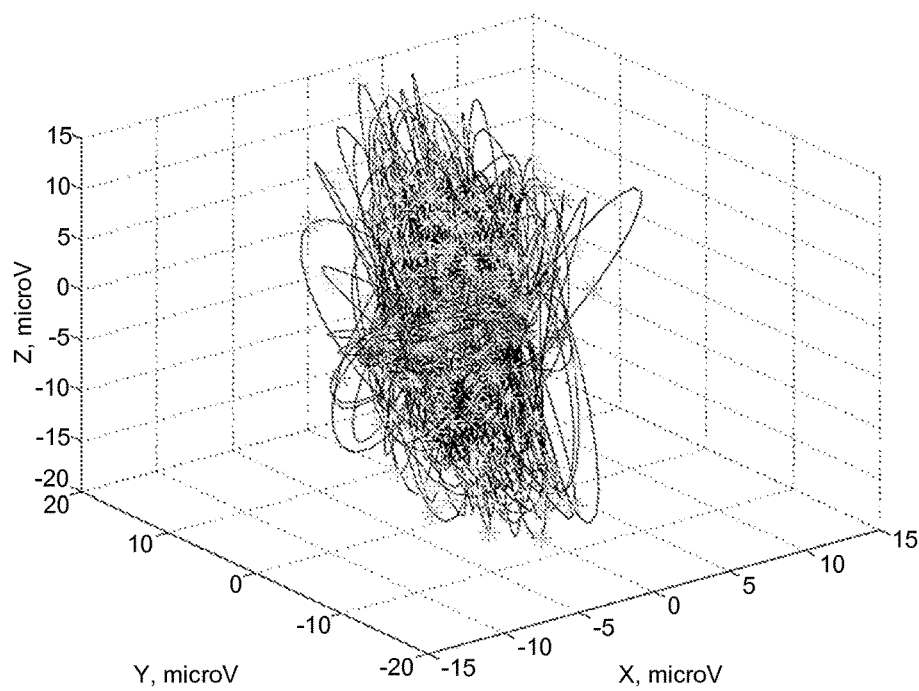
Figure 4K:
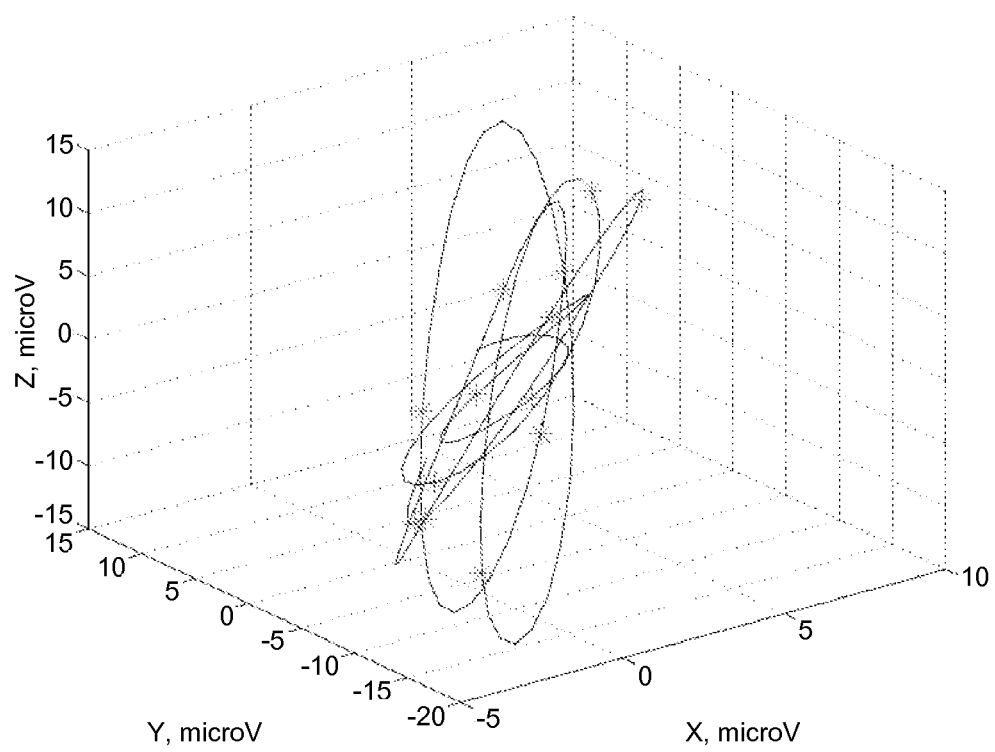

A nested case-control study of the Muerte Subita en Insuficiencia Cardiaca (MUSIC) HF cohort (mean age 63.1±11.7; males 70.6%; LVEF>35% in 48%) was conducted. The conduction pattern in SCD victims was compared with ischemic cardiomyopathy (n=10), non-ischemic cardiomyopathy (n=10), MUSIC study participants, with 10 healthy adults (IDEAL study participants). FIGS. 4A-4K illustrate QRS loops of the data collected during this study. The markers along the QRS loops in FIGS. 4A-4-K are used to identify certain data points on the QRS loops. FIGS. 4A-4C illustrate examples of sinus beats from healthy patients; FIGS. 4D-4H illustrate examples of sinus beats from patients with ischemic cardiomyopathy; and FIGS. 4I-4K illustrate examples of sinus beats from patients with non-ischemic cardiomyopathy. The morphology of the unfiltered sinus QRS loops (illustrated in FIGS. 4A, 4D, and 4I) of all collected beats is consistent and uniform. Narrow band-pass filtering & scanning through frequencies reveals different morphologies of the filtered QRS loops as a manifestation of different paths of inapparent ventricular conduction.

In a healthy person, filtering the ECG data changes the presentation of the QRS loops as illustrated in FIG. 4B, but all consecutive sinus beats remain alike, and 10-ms marks (illustrated by the markers along the path of the QRS loops) are synchronous in all 30 QRS loops. An isolated sinus beat (FIG. 4C) shows rotation in one dominant plane. Filtering the ECG data from the ischemic cardiomyopathy patient (FIG. 4E) uncovers three different conduction patterns, shown as 3 separate beats (FIGS. 4F-4H). All together, the filtered loops from FIG. 4E look like a cloud due to remarkable heterogeneity of conduction beat-to-beat. It is seen that the filtered QRS loops are rotating in multiple planes, illustrating intra-beat and inter-beat heterogeneity of conduction. In the patient with non-ischemic cardiomyopathy only one type of beat is present after filtering the ECG data. The filtered ECG data from the patient with non-ischemic cardiomyopathy is shown in FIG. 4J, while the isolated beat is shown in FIG. 4K. All-together, the 30 filtered QRS loops form a heterogeneous cloud, which illustrates beat-to-beat heterogeneity in cardiac activation in the presence of diffuse interstitial fibrosis.

Experiment #3

Figure 5A:
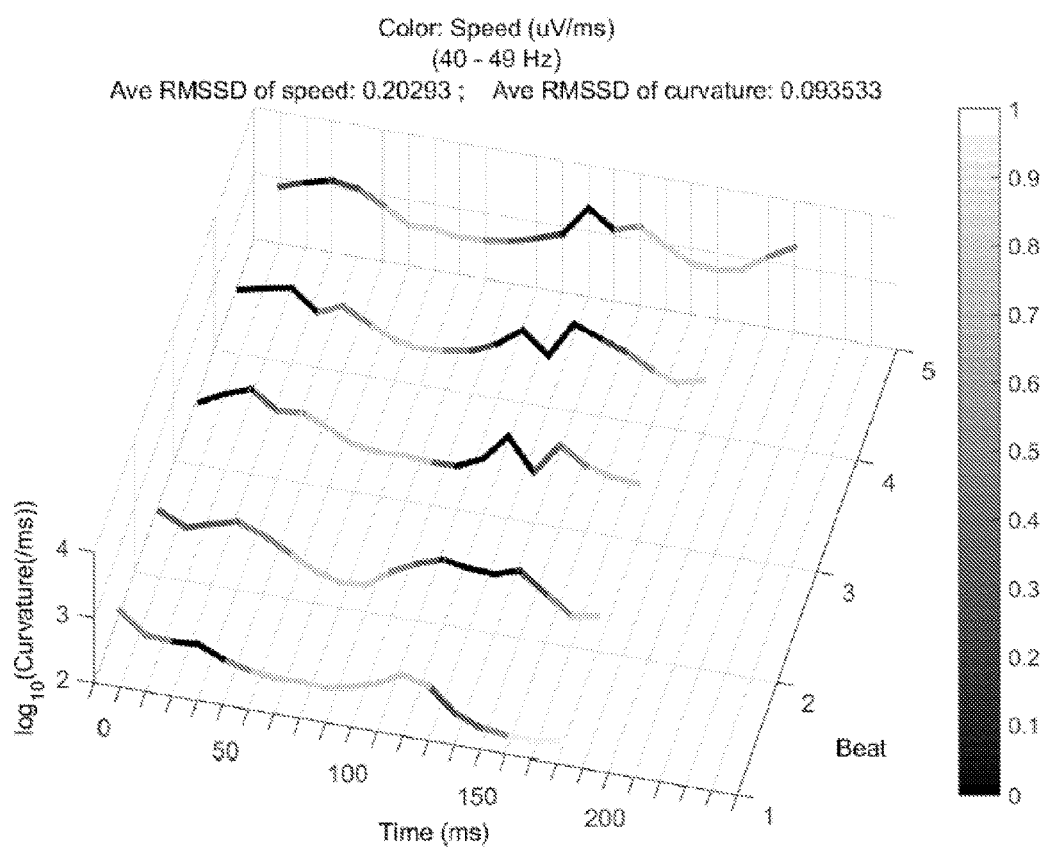
FIGS. 5A-5D illustrate example measured velocities and curvatures of filtered ECG data for patients before and after VT ablation.
Figure 5B:
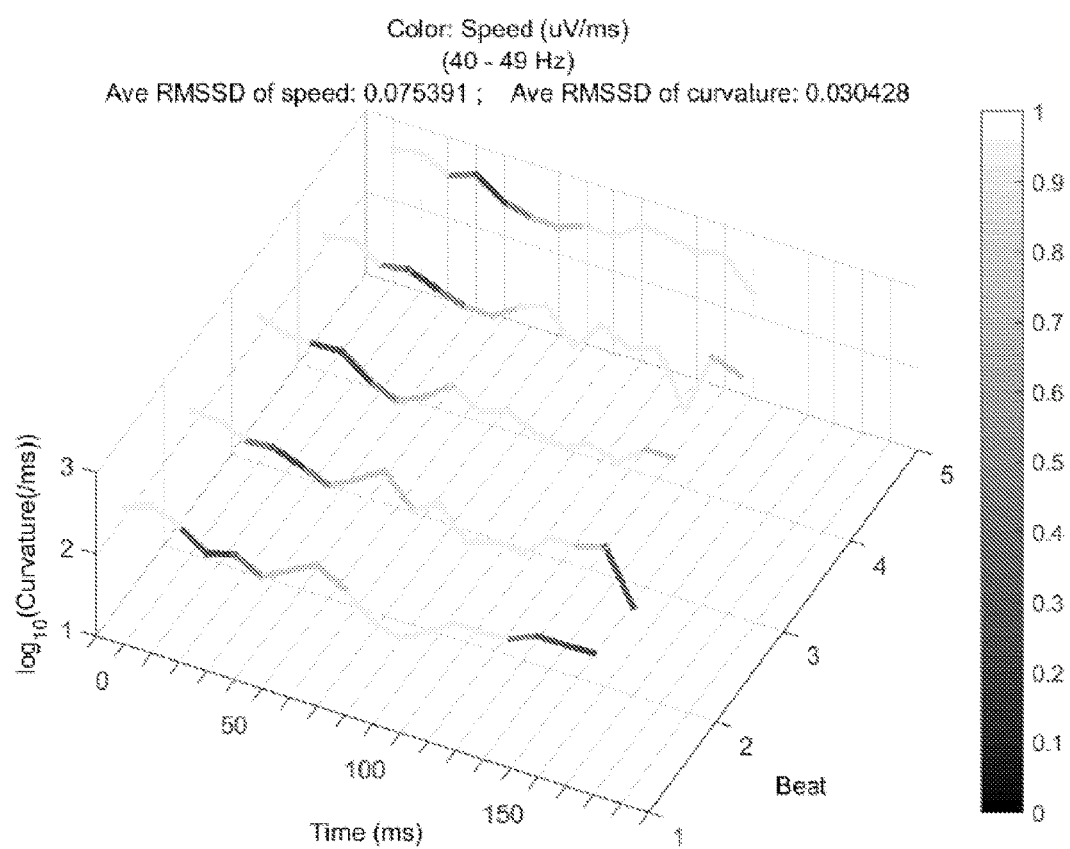
Figure 5C:
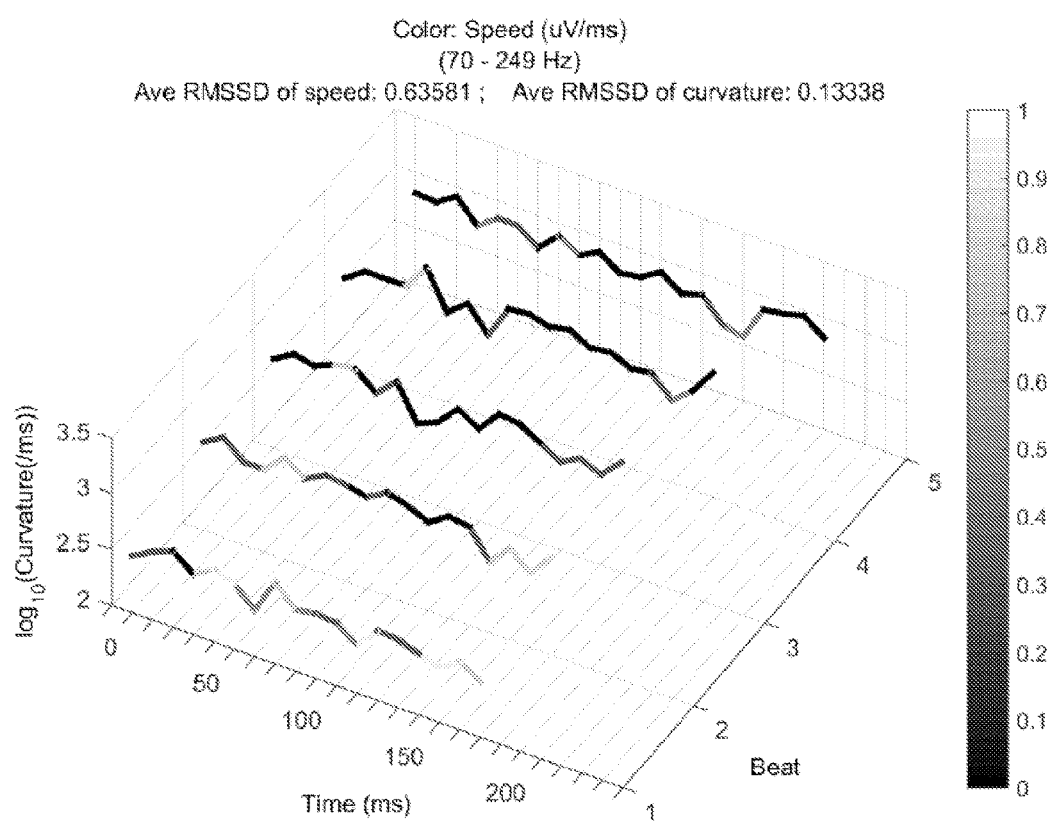
Figure 5D:
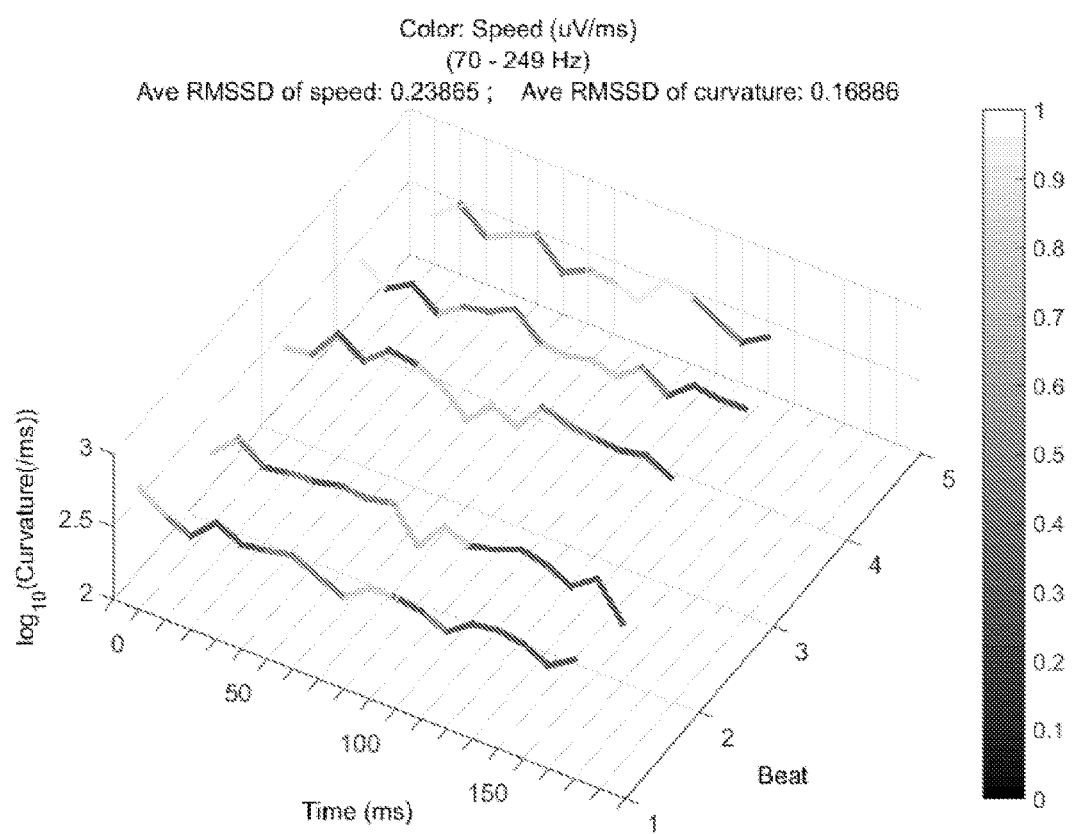

The velocity and curvature of filtered heart vector movement through cardiac cycle during right ventricular pacing (RVP) in sinus rhythm before and after VT ablation was compared. FIG. 5A illustrates the measured velocity of the heart vector filtered between 40-49 Hz before VT ablation, while FIG. 5B illustrates the measured velocity of the heart vector filtered between 40-49 Hz after VT ablation. FIG. 5C illustrates the measured velocity of the heart vector filtered between 70-249 Hz before VT ablation, while FIG. 5D illustrates the measured velocity of the heart vector filtered between 7-249 Hz after VT ablation. The right ventricular paced beats are compared in each case. The average speed of the filtered heart vector movement significantly increased after successful VT ablation (defined as VT-non-inducibility), which suggests that the area of slow conduction was isolated or destroyed during the ablation procedure. This fact also supports the notion that measuring the speed of the filtered heart vector movement indeed reflects ventricular conduction velocity. Homogeneity of the conduction (both intra-beat and inter-beat) after successful VT ablation was significantly improved.

Figure 6A:
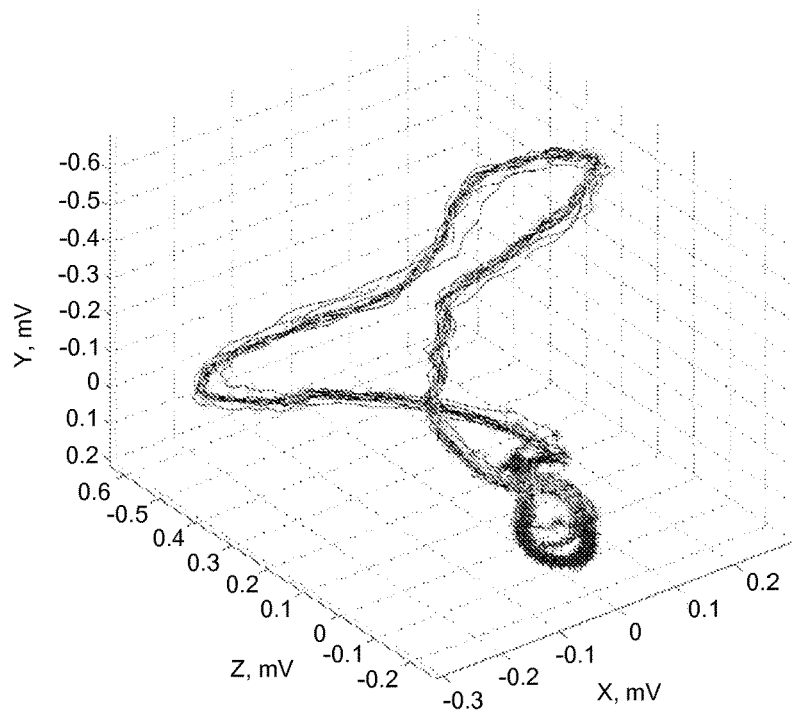
FIGS. 6A-6L illustrate example QRS loops from patients before and after VT ablation.
Figure 6B:
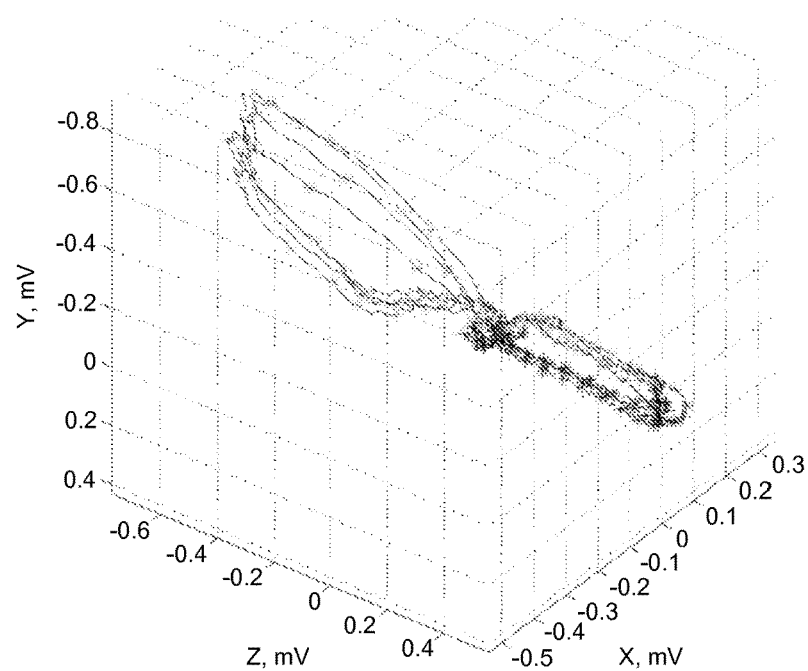
Figure 6C:
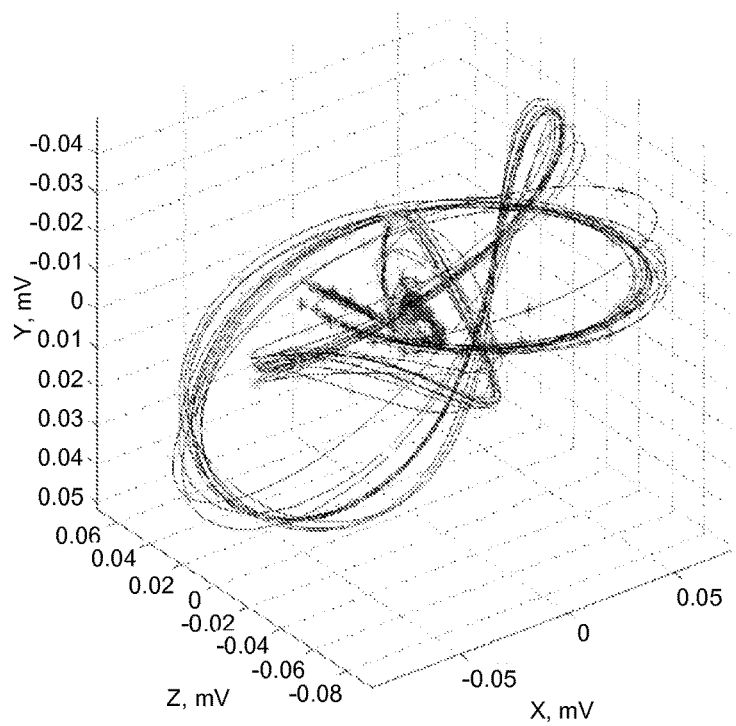
Figure 6D:
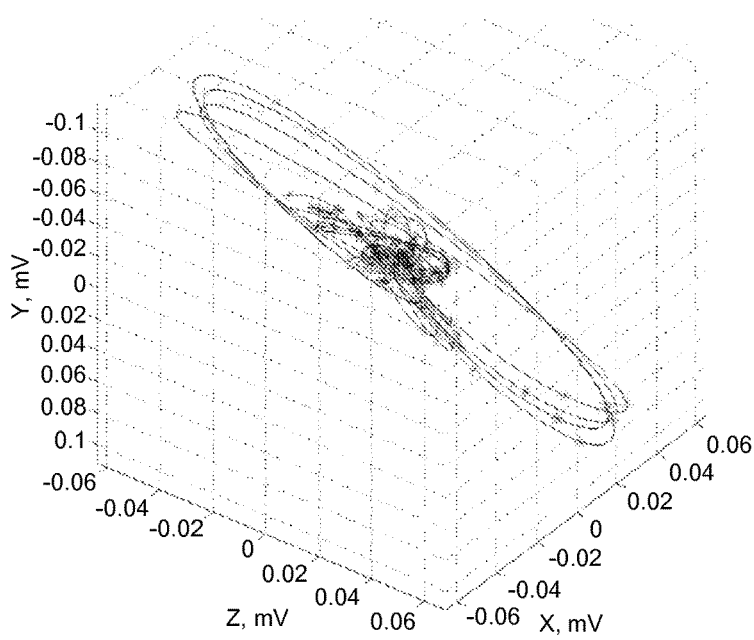
Figure 6E:
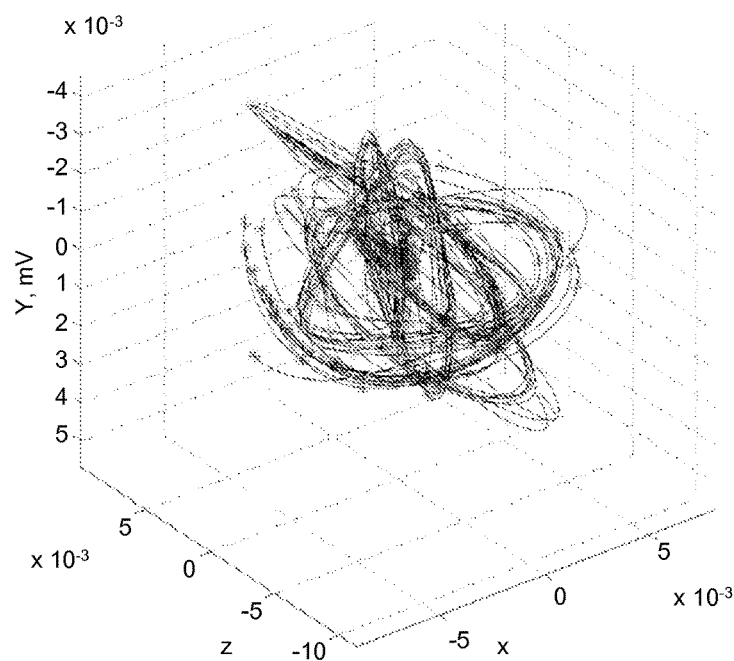
Figure 6F:
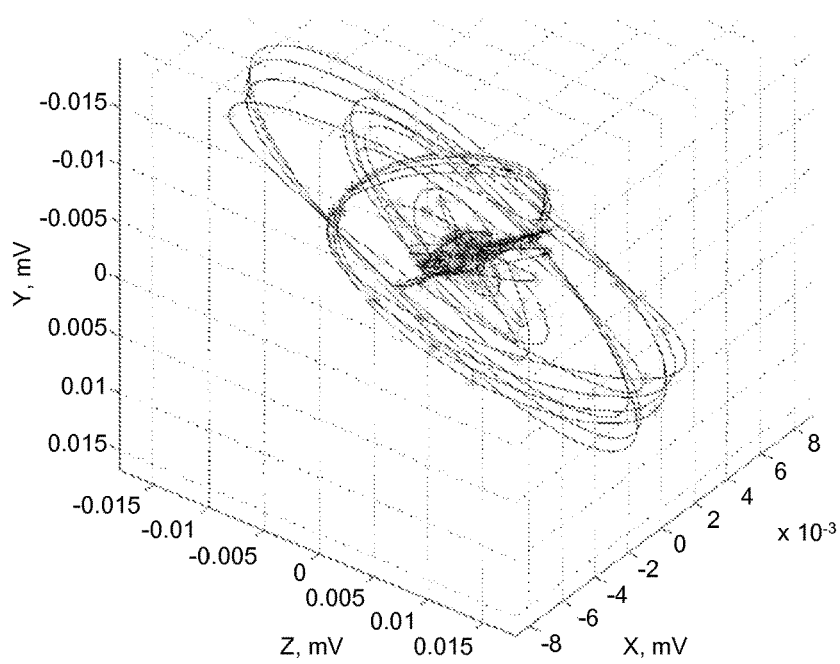
Figure 6G:
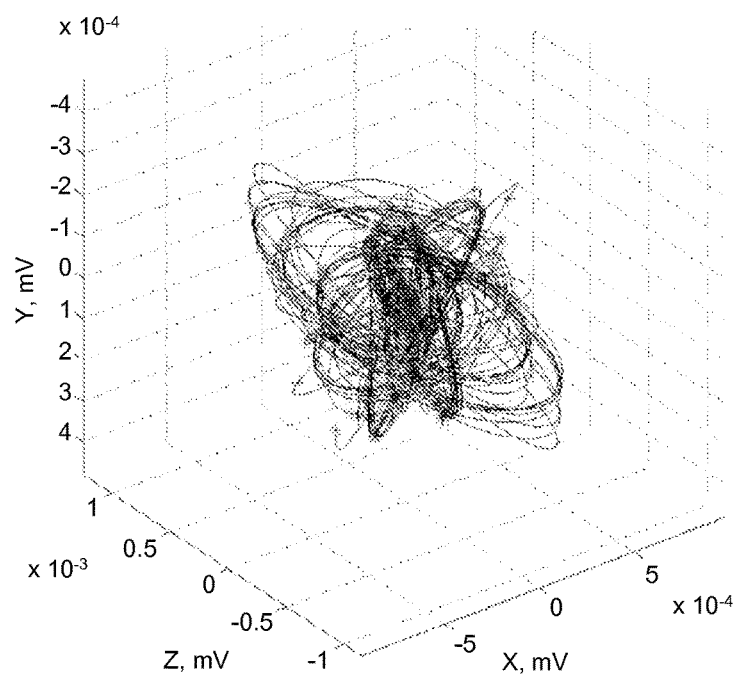
Figure 6H:
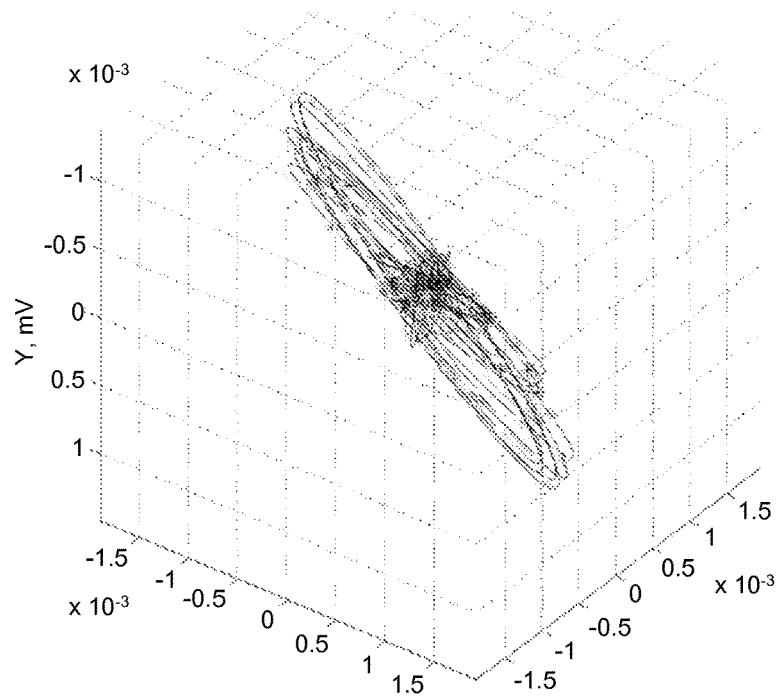
Figure 6I:
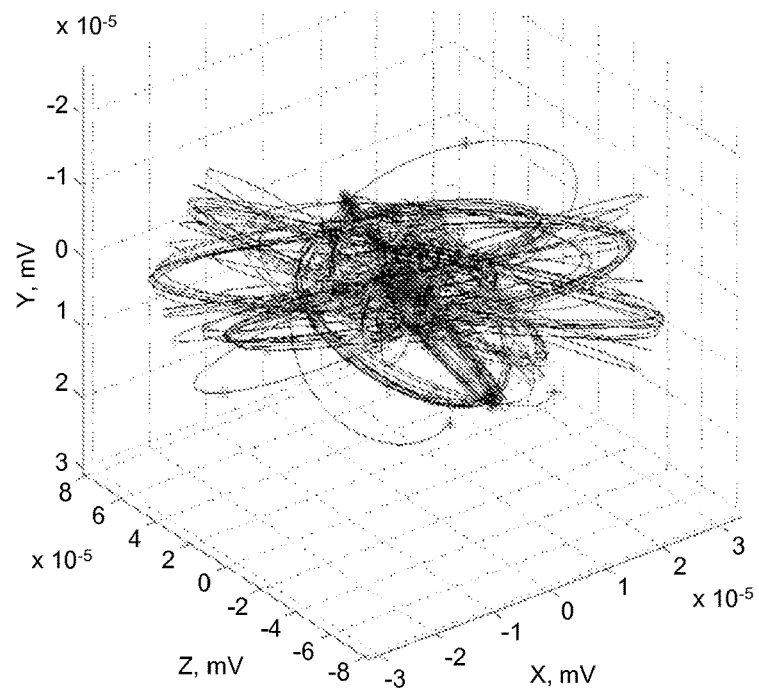
Figure 6J:
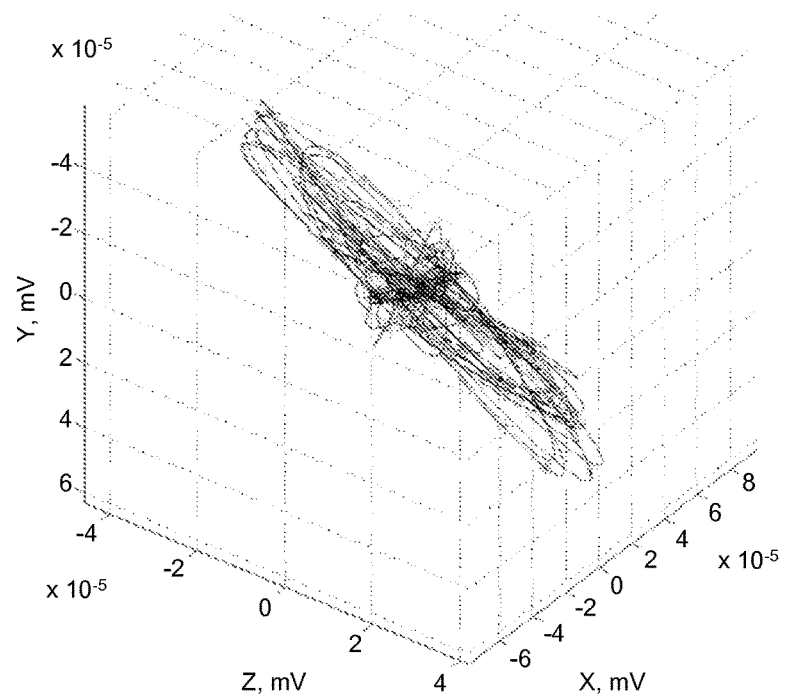
Figure 6K:
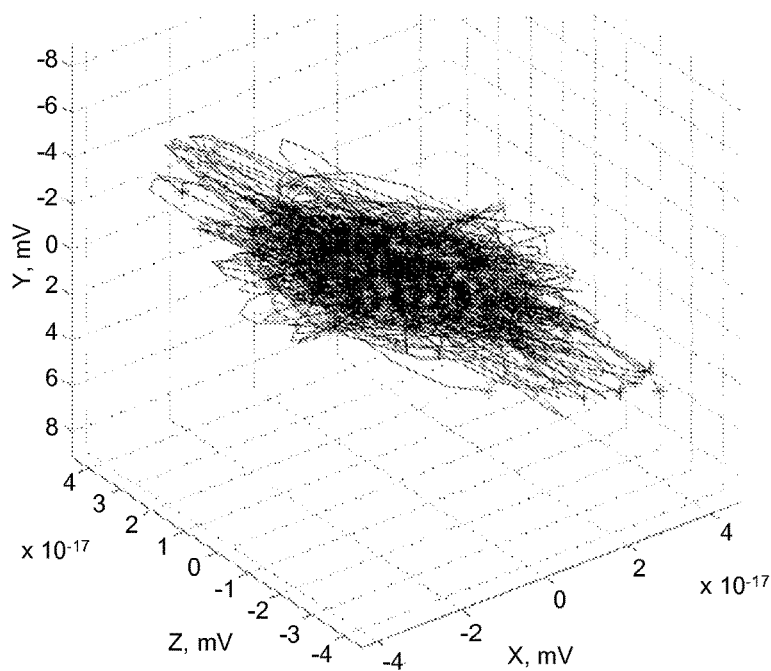
Figure 6L:
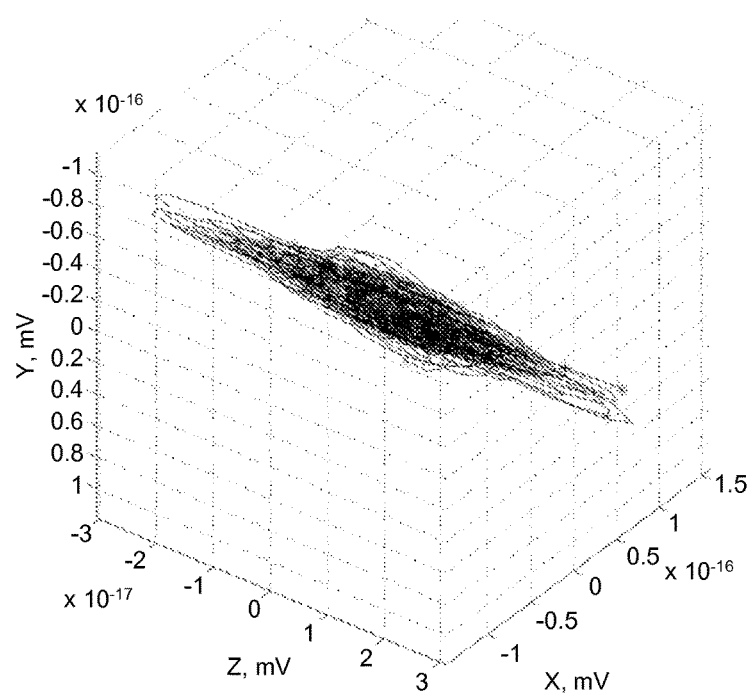

FIGS. 6A-6L illustrate comparisons of RV pacing in sinus rhythm before and after VT ablation at different frequency ranges. The markers along the QRS loops in FIGS. 6A-6L are used to identify certain data points on the QRS loops. FIG. 6A illustrates the unfiltered data before VT ablation while FIG. 6B illustrates the unfiltered data after VT ablation. FIG. 6C illustrates the data filtered between 10-19 Hz before VT ablation while FIG. 6D illustrates the data filtered between 10-19 Hz after VT ablation. FIG. 6E illustrates the data filtered between 20-29 Hz before VT ablation, while FIG. 6F illustrates the data filtered between 20-29 Hz after VT ablation. FIG. 6G illustrates the data filtered between 30-39 Hz before VT ablation, while FIG. 6H illustrates the data filtered between 30-39 Hz after VT ablation. FIG. 6I illustrates the data filtered between 40-49 Hz before VT ablation, while FIG. 6J illustrates the data filtered between 40-49 Hz after VT ablation. FIG. 6K illustrates the data filtered between 70-300 Hz before VT ablation while FIG. 6L illustrates the data filtered between 70-300 Hz after VT ablation. Beats are aligned at the onset of the QRS loop. After VT ablation, the pattern of conduction changes due to electrical isolation or destruction of the VT critical isthmus.

The data illustrated in FIGS. 5A-5D and FIGS. 6A-6L illustrate a comparison of the 3D-morphology of the filtered loops of RV-paced beats, speed and curvature at every 10 ms of the cardiac cycle. The velocity of the filtered heart vector at 40-49 Hz was twice slower at the first 50 ms of the cardiac cycle if VT was inducible: 8.3±3.1 vs. 19.8±10.0 µV/ms; $P<0.00001$. The curvature of the filtered 40-49 Hz loop was 4-fold higher in VT-inducible RVP (103830±66019 vs. 26761±10836; $P<0.00001$). To study beat-to-beat differences in velocity, a longitudinal (panel) analysis was conducted. In a random-effect logistic regression, beat-to-beat progressive slowing of filtered (40-49 Hz) heart vector velocity at first 10 ms of cycle was associated with VT inducibility [β-coeff−1225181 (95% CI−1972071 to −478290); $P=0.001$]. Table 3 below reports selected dynamic predictors of VT-inducibility. The arrows indicate whether the parameter is increasing or decreasing over the given timeframe, and frequency range.

TABLE 3

| Dynamic predictor of inducibility | β-coefficient (95% CI) | P |
|---|---|---|
| ↓speed 10 ms 40-49 Hz | −1225181 (−1972071 to −478290) | 0.001 |
| ↑curvature 30 ms 40-49 Hz | .0002 (0.0001-0.0004) | 0.053 |
| ↓speed 130 ms 10-19 Hz | −5453 (−8688 to −2219) | 0.001 |
| ↓speed 140 ms 10-19 Hz | −10732 (−18558 to −2906) | 0.007 |
| ↓speed 150 ms 10-19 Hz | −9326 (−17699 to −952) | 0.029 |
| ↓speed 240 ms 10-19 Hz | −2379 (−4464 to −294) | 0.025 |
| ↓speed 250 ms 10-19 Hz | −5489 (−10593 to −386) | 0.035 |

Nonparametric analysis of the receiver operating characteristic (ROC) curve under covariates, using bootstrap (1000 replications) showed high accuracy (Area-Under-Curve ROC>0.8) of diagnosing VT-non-inducibility for the selected predictors as shown below in Table 4. Inducible VT was associated with a slower filtered heart vector speed and a larger curvature of the loops through the cardiac cycle.

TABLE 4

| Predictor of inducibility | ROC | 95% CI |
|---|---|---|
| ↓speed 10 ms 40-49 Hz | 0.849 | 0.763-0.935 |
| ↑speed 100 ms 40-49 Hz | 0.822 | 0.731-0.914 |
| ↑curvature 30 ms | 0.859 | 0.784-0.934 |
| ↓speed 10 ms 70-300 Hz | 0.863 | 0.781-0.943 |
| ↓speed 20 ms 70-300 Hz | 0.866 | 0.786-0.947 |
| ↓speed 30 ms 70-300 Hz | 0.879 | 0.805-0.954 |
| ↓speed 40 ms 70-300 Hz | 0.855 | 0.771-0.939 |
| ↓speed 50 ms 70-300 Hz | 0.841 | 0.759-0.923 |
| ↑curvature THRU ALL CYCLE 70-300 Hz | >0.8 | 0.720-0.970 |
| ↑curvature 290 ms 70-300 Hz | 0.902 | 0.841-0.964 |
| ↓speed 100 ms 10-19 Hz | 0.936 | 0.892-0.981 |
| ↓speed 110 ms 10-19 Hz | 0.859 | 0.786-0.932 |
| ↓speed 130 ms 10-19 Hz | 0.959 | 0.926-0.993 |
| ↓speed 140 ms 10-19 Hz | 0.9995 | 0.998-1.00 |
| ↓speed 150 ms 10-19 Hz | 0.967 | 0.936-0.997 |
| ↓speed 170 ms 10-19 Hz | 0.927 | 0.877-0.976 |
| ↓speed 180 ms 10-19 Hz | 0.825 | 0.746-0.904 |
| ↓speed 190 ms 10-19 Hz | 0.854 | 0.781-0.927 |
| ↓speed 200 ms 10-19 Hz | 0.865 | 0.791-0.939 |
| ↓speed 210 ms 10-19 Hz | 0.865 | 0.791-0.939 |
| ↓speed 240 ms 10-19 Hz | 0.837 | 0.741-0.932 |
| ↓speed 250 ms 10-19 Hz | 0.916 | 0.851-0.980 |
| ↓curvature 60 ms 10-19 Hz | 0.958 | 0.903-1.000 |
| ↓curvature 90 ms 10-19 Hz | 0.896 | 0.817-0.974 |
| ↑curvature 130 ms 10-19 Hz | 0.829 | 0.748-0.909 |
| ↑curvature 140 ms 10-19 Hz | 0.919 | 0.822-1.00 |
| ↑curvature 200 ms 10-19 Hz | 0.844 | 0.759-0.930 |
| ↑curvature 240 ms 10-19 Hz | 0.907 | 0.825-0.990 |
| ↑curvature 250 ms 10-19 Hz | 0.959 | 0.914-1.00 |

Experiment #4

Digital ECGs from 81 participants in the Intercity Digital Electrocardiogram Alliance (IDEAL) study were retrospectively analyzed. Of the 81 participants, 13 had myocardial infarction (MI) and primary prevention implantable cardioverter-defibrillators (ICDs). These 13 participants had negative electrophysiology studies and never received appropriate therapy for VT. Another 8 participants had MI and spontaneous and recurrent VT. Digital 12 lead ECGs were used to measure QRS loops from each of the participants. The QRS loops were rotated, translated, and rescaled to remove the effects of respiration, and then filtered at multiple frequency bands between 10-249 Hz. The speed of the heart vector movement was calculated at 10 equal segments normalized to the QRS duration.

Figure 7A:
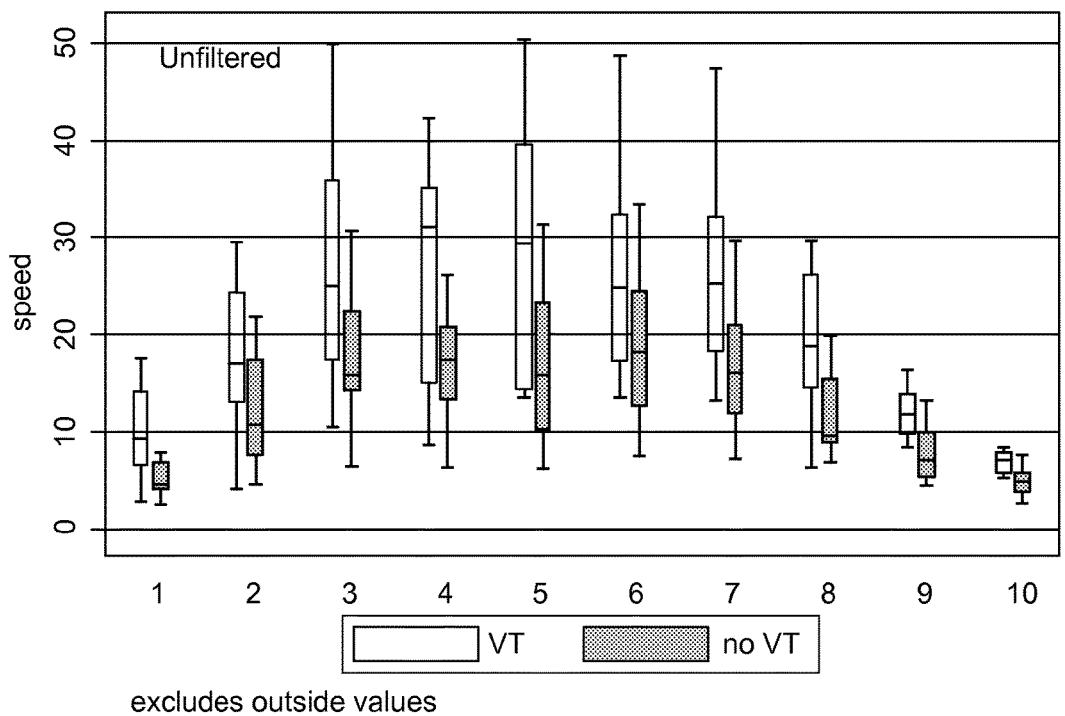
FIGS. 7A-7C illustrate example measured speed of filtered and non-filtered ECG data for patients with and without VT.
Figure 7B:
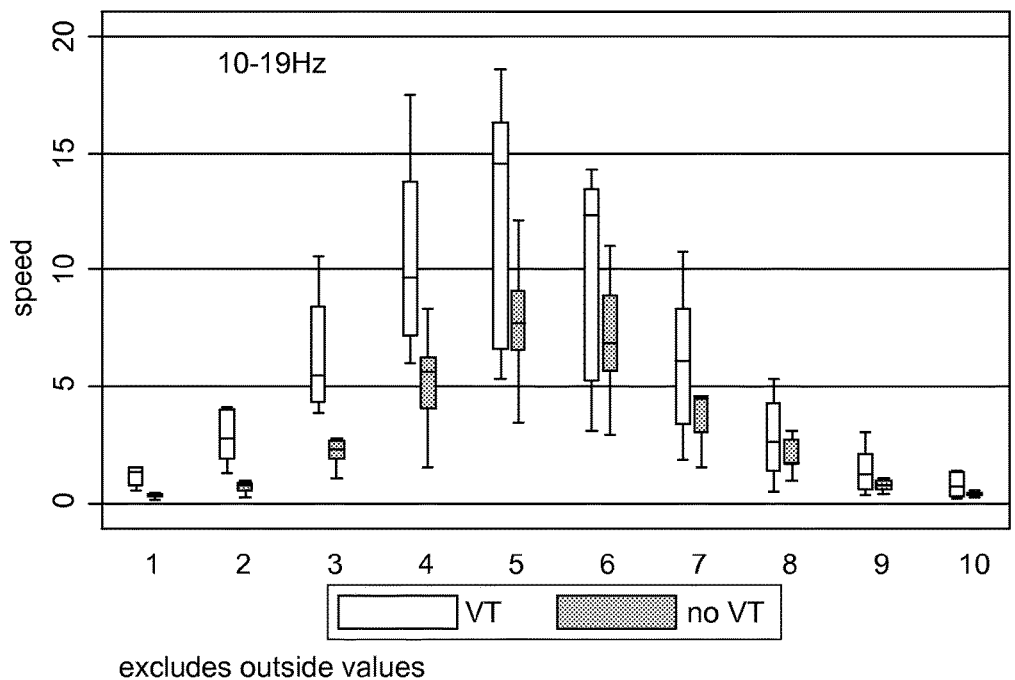
Figure 7C:
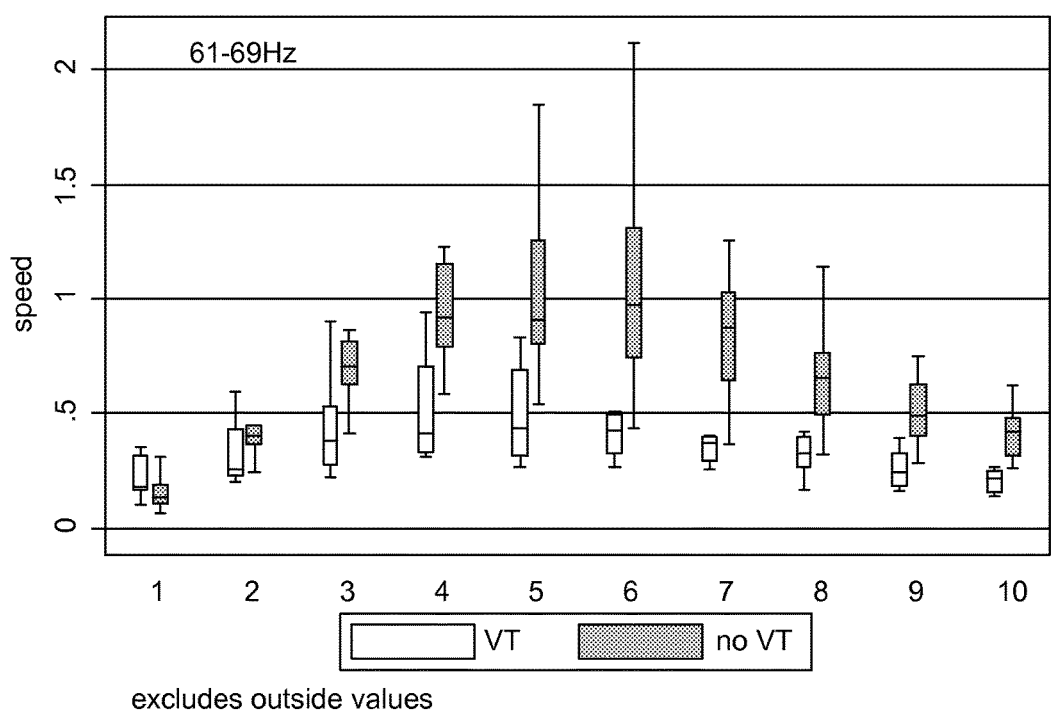

FIGS. 7A-7C illustrate a comparison between the heart vector speed of the MI patients with and without VT, for each segment (1-10) during the QRS duration. FIG. 7A illustrates the measured speed of the unfiltered QRS loops. It is difficult to distinguish between those patients with and without VT using the unfiltered data in any QRS loop segment. FIG. 7B illustrates the measured speed of the QRS loops filtered between 10 and 19 Hz. Here, a more clear difference can be seen between those patients with and without VT in certain QRS segments, such as in segments 1-4. FIG. 7C illustrates the measured speed of the QRS loops filtered between 61 and 69 Hz. Here, a more clear difference is seen in the speed of the QRS loops between those patients with and without VT in most of the QRS segments, such as in segments 3-10.

Example Techniques for Quantifying Heart Vector Curvature and Velocity

Figure 8:
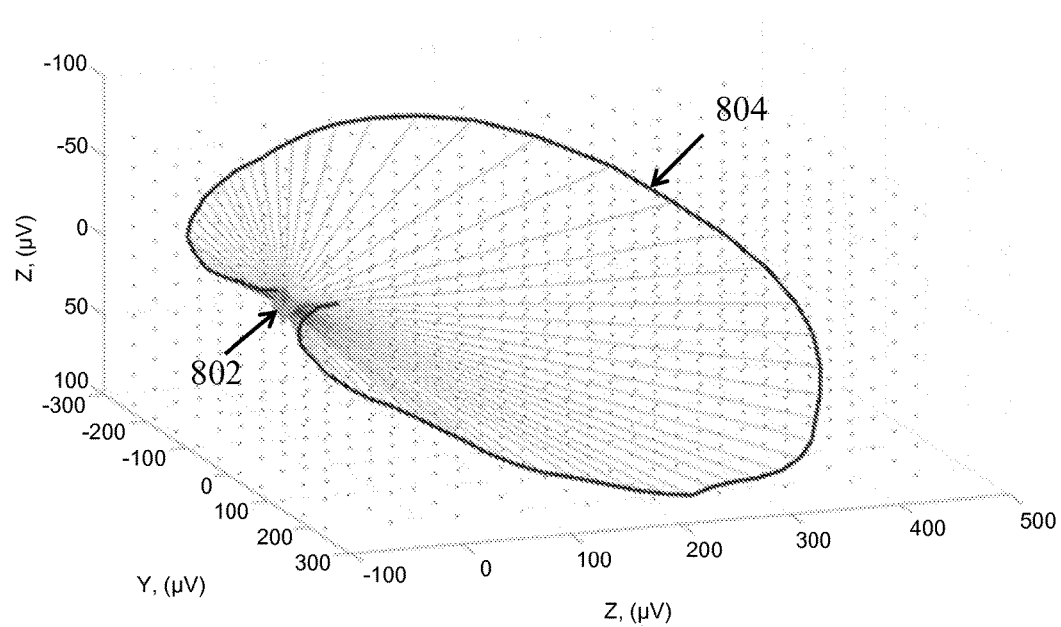
FIG. 8 illustrates a graphical representation of a QRS loop with a geometrical median identified.

Some techniques for quantifying the heart vector curvature or velocity include measuring a dihedral angle or rotational angle, respectively, between adjacent samples of a given QRS loop, according to some embodiments. A minimum of three points are needed to create a plane in Euclidian space. In order to trace changes in the orientation of a plane over time, two consecutive sample points may be selected on a given QRS loop. The third point may be selected by computing the geometrical median (GM), which is defined as the point in space which is derived by minimizing the sum of distances from the other two sample points on the QRS loop as follows:

$$GM = \text{minimum} \Sigma \|VCG_i - GM\| \quad (1)$$

where, $VCG_i$ are the $i^{th}$ XYZ coordinates of the QRS loop in time. Due to the infinite nature of space, this calculation is computationally expensive without restricting the number of potential samples. Consequently, according to an embodiment, a cuboid of 1000 samples is fitted within the minimum and maximum values calculated from each coordinate of the QRS loop. For each sample in the cuboid, the Euclidian distances to all the other samples in the QRS loop are calculated. Subsequently, the sum of all Euclidian distances is determined, and the sample in the cuboid with the smallest sum of Euclidian distances is taken as the geometrical median as shown graphically in FIG. 8. The geometrical median is indicated by marker 802 while the QRS loop is indicated by marker 804.

It should be understood that the third point selected to define a plane in Euclidian space does not need to be the geometrical median. The third point may also be the origin of the QRS loop. In another example, the third point is any arbitrary point along the QRS loop. The third point may also be any arbitrary point in Euclidian space, so long as the same third point is used to define each plane between adjacent samples of the QRS loop.

Vectors are drawn (as straight lines) from the third point to sample points on the QRS loop. Vectors obtained in this way are defined as loop vectors. Consecutive QRS loop vectors ($V_n$ and $V_{n+1}$), using the geometrical median (GM) as the third point, may be used to define a plane ($P_n$) as follows:

$$V_n = VCG_n - GM, \quad (2)$$
$$V_{n+1} = VCG_{n+1} - GM;$$

$$P_n = \vec{V_n} \times \vec{V_{n+2}}$$

Figure 9:
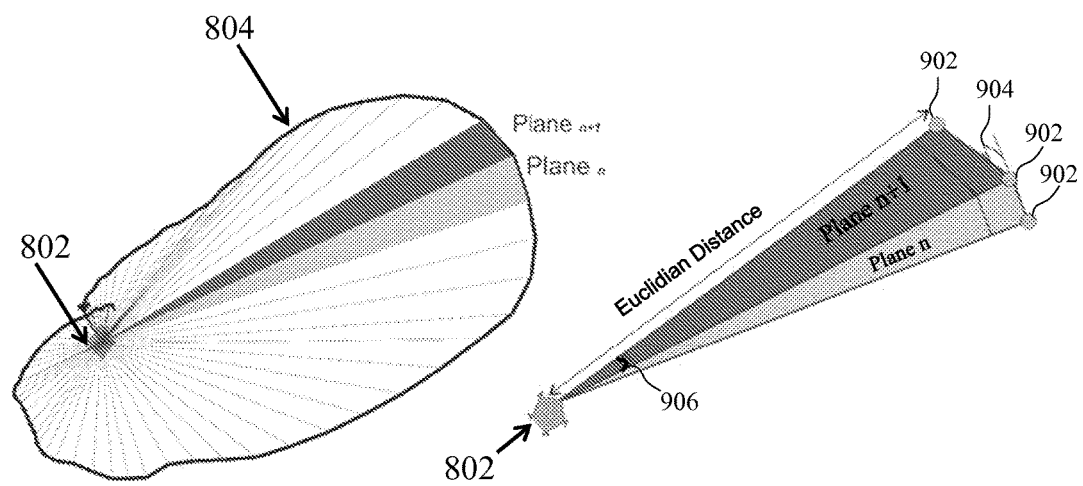
FIG. 9 illustrates a graphical representation of a QRS loop with dihedral angle and rotation angle identified.

Planes may be defined between two consecutive samples 902 of a QRS loop 804 and the geometrical median 802 as illustrated in FIG. 9. The dihedral angle ($\theta_k$) between two consecutive planes ($P_n$ and $P_{n+1}$) may be calculated as follows:

$$\theta_k = \cos^{-1}\left(\frac{Pn \cdot Pn+1}{|Pn||Pn+1|}\right) \quad (3)$$

$$k = 1, 2, 3 \ldots n-1$$

Figure 10A:
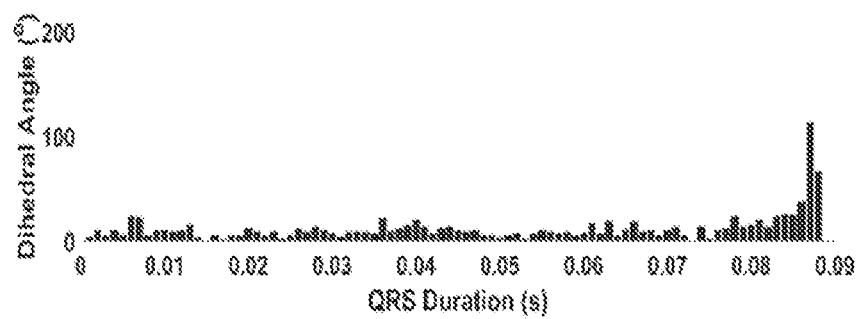
FIGS. 10A and 10B illustrate example dihedral angles of QRS vectors over time.
Figure 10B:
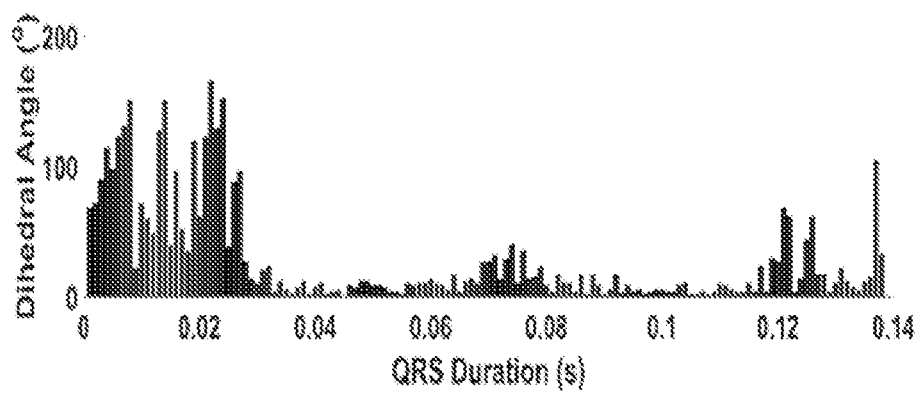

The calculated dihedral angle between two planes is shown graphically in FIG. 9 as marker 904. The computed dihedral angles for a single QRS complex (made up of multiple QRS loops) may be plotted to observe the variation in the QRS loop movement within a given planar surface over time. Example plots of the dihedral angle over QRS duration are shown in FIGS. 10A and 10B. FIG. 10A shows the dihedral angle plotted for a healthy patient while FIG. 10B shows the dihedral angle plotted for a patient with post-infarct monomorphic VT, undergoing VT ablation. Changes in dihedral angle among patients with VT are abrupt and demonstrate less planarity compared to those among healthy patients. The sudden changes in dihedral angle may be visually identified as a fold in the plotted QRS loop. The mean dihedral angle may be calculated for each QRS complex to assess the overall planar variation of the QRS loop over time.

A rotation angle may be measured as the angle between two consecutive loop vectors and used as a way of quantifying the velocity of the heart vector, according to an embodiment. A calculated rotation angle between two consecutive loop vectors is shown graphically in FIG. 9 as marker 906. The cumulative rotation angle may be derived by successive addition of rotation angles, starting from the QRS loop onset. The cumulative rotation angle may be used to count the number of QRS loops in one QRS complex by dividing the sum of angles by $2\pi$. The linearity of the cumulative rotation of each QRS complex may be calculated by fitting a polynomial of first degree.

Figure 11A:
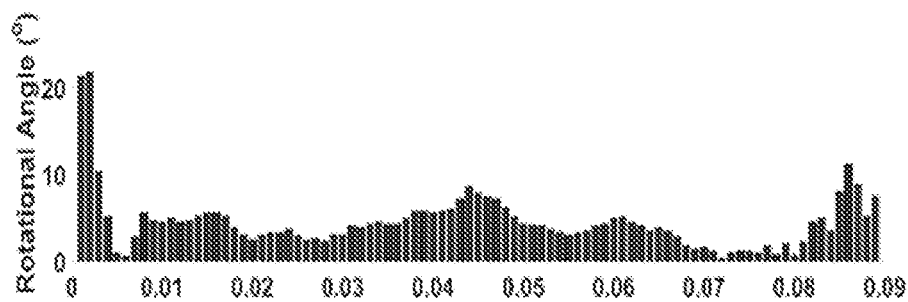
FIGS. 11A and 11B illustrate example rotation angles of QRS vectors over time.
Figure 11B:
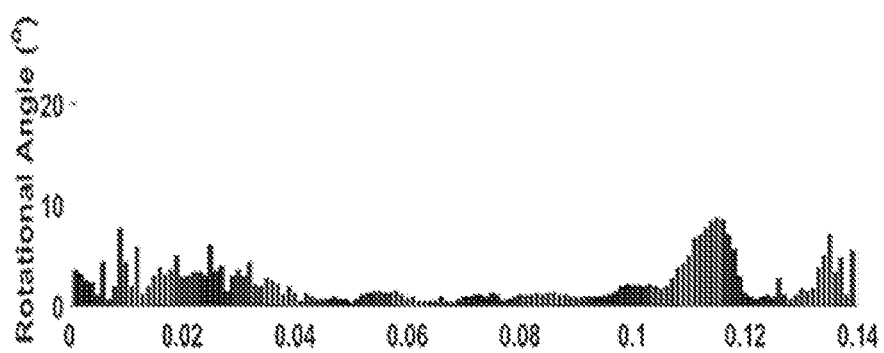

FIGS. 11A and 11B illustrate example plots of the rotation angle over time. FIG. 11A shows the rotation angle plotted for a healthy patient while FIG. 11B shows the rotation angle plotted for a patient with post-infarct monomorphic VT, undergoing VT ablation. As shown in FIGS. 11A and 11B, rotational angles had abrupt changes during the QRS loop in VT cases which caused multiple phases and nonlinearity in cumulative rotation. For the healthy patients, the rotational angle changes were smooth over the entire QRS duration.

Clinical Significance

The embodiments of the present application for identifying risk of ventricular tachycardia may be used for risk stratification of sudden cardiac death (SCD). The analysis of speed and curvature of filtered QRS loops can more accurately identify individuals at the highest risk of SCD, and who would benefit the most from primary prevention implantable cardioverter-defibrillators (ICDs). The analysis may be performed with a standard 12-lead ECG, providing a widely available and inexpensive tool for identifying high-risk individuals in the most need for urgent care.

Embodiments of the present application may also be used for medium-term prediction of sustained ventricular arrhythmia with appropriate ICD therapy (e.g., shock or anti-tachycardia pacing). For medium-term prediction, data may be received from intracardiac electrograms (e.g., from implanted electrodes). A transformation matrix may be used for construction of intracardiac vectorcardiographic loops out of the intracardiac electrograms. Medium-term prediction of sustained ventricular arrhythmia can enable preventive interventions through evaluation by a cardiologist or electrophysiologist, and individualized patient management (e.g., coronary revascularization, adjustment of heart failure medications, adjustment of the dosage of anti-arrhythmic drugs, etc). Timely and accurate middle-term prediction of impending ventricular arrhythmia is clinically important as it helps to avoid ICD shocks, which are known to have deleterious consequences (e.g., heart failure exacerbation, heart failure death, psychological post-ICD shock syndrome, etc).

Embodiments of the present application may also be used to help guide tachyarrhythmia (e.g., ventricular tachycardia or atrial fibrillation) ablation. QRS loops may be constructed from bipolar or unipolar electrograms recorded by a mapping catheter during endocardial or epicardial mapping. The data may then be filtered at a given frequency bandwidth to build an activation map, which helps to characterize the cardiac activation.

Final Remarks

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for identifying a risk of ventricular tachycardia in a patient, comprising:
    receiving ECG signals from the patient;
    filtering the ECG signals to generate filtered ECG signals;
    identifying, in real-time, a heart vector from the filtered ECG signals;
    measuring, in real-time, a velocity of the heart vector;
    quantifying, in real-time, a change in curvature of the identified heart vector; localizing, in real-time, an origin of arrhythmia in the patient; and
    determining, in real-time, the risk of ventricular tachycardia based at least on the measured velocity and the quantified change in curvature of the identified heart vector.

2. The method of claim 1, wherein the receiving the ECG signals comprises receiving ECG signals from a standard 12-lead ECG.

3. The method of claim 1, wherein the receiving the ECG signals comprises receiving ECG signals from a set of XYZ leads.

4. The method of claim 1, wherein the receiving the ECG signals comprises receiving ECG signals across at least two consecutive heart beats of the patient.

5. The method of claim 1, wherein the filtering the ECG signals comprises filtering within a frequency range having a passband of about 10 Hz.

6. The method of claim 1, further comprising displaying the filtered ECG signals.

7. The method of claim 6, wherein the displaying the filtered ECG signals comprises displaying the filtered ECG signals in three dimensions.

8. The method of claim 1, further comprising identifying one or more cardiac ablation sites based at least on the measured velocity and the quantified change in curvature of the identified heart vector.

9. The method of claim 1, further comprising measuring surface body potentials.

10. The method of claim 9, wherein the determining the risk of ventricular tachycardia further comprises determining the risk of ventricular tachycardia based on the surface body potentials.

11. The method of claim 1, wherein the receiving the ECG signals comprises receiving the ECG signals in real time.

12. The method of claim 1, wherein the receiving the ECG signals comprises receiving the ECG signals from a storage device, the ECG signals having been previously collected from the patient and stored on the storage device.

13. The method of claim 1, wherein the measuring the velocity comprises measuring a rotation angle between consecutive samples of the filtered ECG signals in three dimensions.

14. The method of claim 1, wherein the quantifying the change in curvature comprises measuring a dihedral angle from the filtered ECG signals in three dimensions.

15. The method of claim 1, further comprising:
    measuring an orbital frequency by taking a product of the velocity and the change in curvature, wherein the determining further comprises determining the risk of ventricular tachycardia based on the orbital frequency.

16. A system comprising:
    an input module configured to receive ECG signals related to a patient;
    a filtering module configured to filter the received ECG signals to generate filtered ECG signals; and
    a processor configured to, in real-time:
        identify a heart vector from the filtered ECG signals, and measure a velocity of the heart vector,
        quantify a change in curvature of the identified heart vector, localize an origin of arrhythmia in the patient; and determine a risk of ventricular tachycardia based at least on the measured velocity and the quantified change in curvature of the identified heart vector.

17. The system of claim 16, further comprising a standard 12-lead ECG configured to interface with the input module.

18. The system of claim 16, further comprising a set of XYZ leads configured to interface with the input module.

19. The system of claim 16, wherein the processor is configured to identify the heart vector and measure the velocity of the heart vector across at least two consecutive beats of the patient.

20. The system of claim 16, wherein the filtering module is configured to filter the received ECG signals within a frequency range having a passband of about 10 Hz.

21. The system of claim 16, further comprising a display configured to display the filtered ECG signals.

22. The system of claim 21, wherein the filtered ECG signals are displayed in three spatial dimensions.

23. The system of claim 16, wherein the processor is further configured to identify one or more cardiac ablation sites based at least on the measured velocity and the quantified change in curvature of the identified heart vector.

24. The system of claim 16, wherein the input module comprises a plurality of leads configured to collect surface body potentials from the patient.

25. The system of claim 16, wherein the processor is configured to measure the velocity of the heart vector by measuring a rotation angle between consecutive samples of the filtered ECG signals in three dimensions.

26. The system of claim 16, wherein the processor is configured to quantify the change in curvature by measuring a dihedral angle from the filtered ECG signals in three dimensions.

27. The system of claim 16, wherein the processor is further configured to measure an orbital frequency by taking a product of the velocity and the change in curvature.

28. A computer program product stored on a non-transitory computer-readable medium, including instructions that, when executed by a computing device, cause the computing device to perform, in real-time, one or more functions, comprising:
receiving ECG signals;
identifying a heart vector from filtered ECG signals, wherein the filtered ECG signals are generated by filtering the ECG signals, and measuring a velocity of the heart vector;
quantifying a change in curvature of the identified heart vector; localizing an origin of arrhythmia in the patient; and
determining a risk of ventricular tachycardia based at least on the measured velocity and the quantified change in curvature of the identified heart vector.

* * * * *

UNITED STATES PATENT AND TRADEMARK OFFICE
CERTIFICATE OF CORRECTION

PATENT NO. : 10,517,494 B2
APPLICATION NO. : 15/522615
DATED : December 31, 2019
INVENTOR(S) : Tereshchenko et al.

It is certified that error appears in the above-identified patent and that said Letters Patent is hereby corrected as shown below:

In the Specification

In Column 1, Lines 10-12, replace "This invention was made with government support under Grant No. HL118277 awarded by the National. Institutes of Health" with --This invention was made with government support under Grant No. HL118277 awarded by the National Institutes of Health--.

In the Claims

In Column 16, Lines 5-7, replace "quantifying, in real-time, a change in curvature of the identified heart vector; localizing, in real-time, an origin of arrhythmia in the patient; and" with
--quantifying, in real-time, a change in curvature of the identified heart vector;
localizing, in real-time, an origin of arrhythmia in the patient; and--.

In Column 18, Lines 20-22, replace "quantifying a change in curvature of the identified heart vector; localizing an origin of arrhythmia in the patient; and" with
--quantifying a change in curvature of the identified heart vector;
localizing an origin of arrhythmia in the patient; and--.

Signed and Sealed this
Seventeenth Day of August, 2021

Drew Hirshfeld
*Performing the Functions and Duties of the
Under Secretary of Commerce for Intellectual Property and
Director of the United States Patent and Trademark Office*